(12) United States Patent
Haynie

(10) Patent No.: US 7,888,316 B2
(45) Date of Patent: *Feb. 15, 2011

(54) POLYPEPTIDE FILMS AND METHODS

(75) Inventor: Donald T. Haynie, Tampa, FL (US)

(73) Assignee: Artificial Cell Technologies, Inc., New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/757,085

(22) Filed: Apr. 9, 2010

(65) Prior Publication Data

US 2010/0247633 A1 Sep. 30, 2010

Related U.S. Application Data

(63) Continuation of application No. 12/060,914, filed on Apr. 2, 2008, now Pat. No. 7,723,294.

(60) Provisional application No. 60/909,568, filed on Apr. 2, 2007.

(51) Int. Cl.
 *A61K 38/00* (2006.01)
(52) U.S. Cl. ......................................................... 514/2
(58) Field of Classification Search ........................ None
 See application file for complete search history.

(56) References Cited

U.S. PATENT DOCUMENTS 5,629,213 A    5/1997   Kornguth et al.
5,981,170 A   11/1999   Trojnar et al.
6,689,478 B2   2/2004   Laguitton
2004/0241202 A1 12/2004  Chluba et al.
2005/0069950 A1  3/2005  Haynie

FOREIGN PATENT DOCUMENTS

WO    9308766 A1    5/1993

OTHER PUBLICATIONS

Chluba, et al; "Peptide Hormone Covalently Bound to Polyelectrolytes and Embedded into Multilayer Architectures Conserving Full Biological Activity"; Biomacromolecules; 2; pp. 800-805; (2001).
Chou, et al; "Conformational Parameters for Amino Acids in Helical, B-Sheet, and Random Coil Regions Calculated from Proteins"; Biochemistry; 13; pp. 211-222; (1974).
Picart et al; "Buildup Mechanism for Poly(L-lysine)/Hyaluronic Acid Films onto a Solid Surface"; Langmuir; 17; pp. 7414-7424; (2001).
Picart, et al; "Molecular Basis for the Explanation of the Exponential Growth of Polyelectrolyte Multilayers"; PNAS; 22; pp. 12531-12535; 2002.

*Primary Examiner*—Christina Bradley
(74) *Attorney, Agent, or Firm*—Cantor Colburn LLP

(57) ABSTRACT

Disclosed herein are polypeptide multilayer films comprising a hybrid polypeptide comprising a first polypeptide segment and a second segment, the two segments being covalently joined by one or more non-peptidic linkages. The first segment comprises a polypeptide having a magnitude of net charge per residue of greater than or equal to 0.4, and a length of greater than or equal to about 12 amino acid residues. The second segment comprises a polypeptide or another polyelectrolyte.

14 Claims, 6 Drawing Sheets

```
SEQUENCE LISTING

<160> NUMBER OF SEQ ID NOS: 15

<210> SEQ ID NO 1
<211> LENGTH: 5
<212> TYPE: PRT
<213> ORGANISM: Artificial Sequence
<220> FEATURE:
<223> OTHER INFORMATION: factor Xa recognition sequence

<400> SEQUENCE: 1

Ile Glu Asp Gly Arg
1               5

<210> SEQ ID NO 2
<211> LENGTH: 5
<212> TYPE: PRT
<213> ORGANISM: Artificial Sequence
<220> FEATURE:
<223> OTHER INFORMATION: enterokinase recognition sequence

<400> SEQUENCE: 2

Asp Asp Asp Asp Lys
1               5

<210> SEQ ID NO 3
<211> LENGTH: 6
<212> TYPE: PRT
<213> ORGANISM: Artificial Sequence
<220> FEATURE:
<223> OTHER INFORMATION: thrombin recognition sequence

<400> SEQUENCE: 3
```

-continued

Leu Val Pro Arg Gly Ser
1               5

<210> SEQ ID NO 4
<211> LENGTH: 7
<212> TYPE: PRT
<213> ORGANISM: Artificial Sequence
<220> FEATURE:
<223> OTHER INFORMATION: TEV protease recognition sequence

<400> SEQUENCE: 4

Glu Asn Leu Tyr Phe Gln Gly
1               5

<210> SEQ ID NO 5
<211> LENGTH: 8
<212> TYPE: PRT
<213> ORGANISM: Artificial Sequence
<220> FEATURE:
<223> OTHER INFORMATION: PreScissionT protease recognition sequence

<400> SEQUENCE: 5

Leu Glu Val Leu Phe Gln Gly Pro
1               5

<210> SEQ ID NO 6
<211> LENGTH: 6
<212> TYPE: PRT
<213> ORGANISM: Artificial Sequence
<220> FEATURE:
<223> OTHER INFORMATION: ECM recognition sequence
<220> FEATURE:
<221> NAME/KEY: X
<222> LOCATION: (3)..(3)
<223> OTHER INFORMATION: hydroxyproline

<400> SEQUENCE: 6

Gly Phe Xaa Gly Glu Arg
1               5

<210> SEQ ID NO 7
<211> LENGTH: 6
<212> TYPE: PRT
<213> ORGANISM: Artificial Sequence
<220> FEATURE:
<223> OTHER INFORMATION: ECM recognition sequence
<220> FEATURE:
<221> NAME/KEY: X
<222> LOCATION: (3)..(3)
<223> OTHER INFORMATION: hydroxyproline

<400> SEQUENCE: 7

Gly Leu Xaa Gly Glu Arg
1               5

<210> SEQ ID NO 8
<211> LENGTH: 6
<212> TYPE: PRT
<213> ORGANISM: Artificial Sequence
<220> FEATURE:
<223> OTHER INFORMATION: ECM recognition sequence

<400> SEQUENCE: 8

Gly Ala Ser Gly Glu Arg
1               5

<210> SEQ ID NO 9

```
<211> LENGTH: 8
<212> TYPE: PRT
<213> ORGANISM: Artificial Sequence
<220> FEATURE:
<223> OTHER INFORMATION: cation binding domain

<400> SEQUENCE: 9

Val Ser Phe Ala Ser Ser Gln Gln
1               5

<210> SEQ ID NO 10
<211> LENGTH: 17
<212> TYPE: PRT
<213> ORGANISM: Gallus gallus

<400> SEQUENCE: 10

Ile Ser Gln Ala Val His Ala Ala His Ala Glu Ile Asn Glu Ala Gly
1               5                   10                  15

Arg

<210> SEQ ID NO 11
<211> LENGTH: 14
<212> TYPE: PRT
<213> ORGANISM: Homo sapiens

<400> SEQUENCE: 11

Phe Glu Pro Ser Glu Ala Glu Ile Ser His Thr Gln Lys Ala
1               5                   10

<210> SEQ ID NO 12
<211> LENGTH: 10
<212> TYPE: PRT
<213> ORGANISM: Mus musculus

<400> SEQUENCE: 12

Glu Cys Glu Ser Ala Glu Thr Thr Glu Asp
1               5                   10

<210> SEQ ID NO 13
<211> LENGTH: 18
<212> TYPE: PRT
<213> ORGANISM: Artificial Sequence
<220> FEATURE:
<223> OTHER INFORMATION: Charged sequence

<400> SEQUENCE: 13

Glu Glu Glu Glu Glu Glu Glu Glu Glu Cys Glu Glu Glu Glu Glu
1               5                   10                  15

Glu Glu

<210> SEQ ID NO 14
<211> LENGTH: 24
<212> TYPE: DNA
<213> ORGANISM: Artificial Sequence
<220> FEATURE:
<223> OTHER INFORMATION: polynucleotide segment

<400> SEQUENCE: 14
actcgcgcgc gcgcgcgcgc cact                                          24

<210> SEQ ID NO 15
<211> LENGTH: 15
<212> TYPE: PRT
<213> ORGANISM: Artificial Sequence
<220> FEATURE:
```

-continued

```
<223> OTHER INFORMATION: charged sequence

<400> SEQUENCE: 15

Lys Lys Lys Lys Lys Lys Lys Lys Lys Lys Lys Lys Lys Lys Lys
1               5                   10                  15
```

POLYPEPTIDE FILMS AND METHODS

CROSS-REFERENCE TO RELATED APPLICATION

This application is a continuation of U.S. application Ser. No. 12/060,914, filed Apr. 2, 2008, which claims the benefit of U.S. Provisional Application No. 60/909,568 filed Apr. 2, 2007, which is incorporated by reference herein in its entirety.

BACKGROUND

Polyelectrolyte multilayer films are thin films (e.g., a few nanometers to millimeters thick) composed of alternating layers of oppositely charged polyelectrolytes. Such films can be formed by layer-by-layer assembly on a suitable substrate. In electrostatic layer-by-layer self-assembly ("ELBL"), the physical basis of association of polyelectrolytes is electrostatics. Film buildup is possible because the sign of the surface charge density of the film reverses on deposition of successive layers. The general principle of ELBL deposition of oppositely charged polyions is illustrated in FIG. 1. The generality and relative simplicity of the ELBL film process permits the deposition of many different types of polyelectrolytes onto many different types of surfaces. Polypeptide multilayer films are a subset of polyelectrolyte multilayer films, comprising at least one layer comprising a charged polypeptide. A key advantage of polypeptide multilayer films is environmental benignity. ELBL films can also be used for encapsulation. Applications of polypeptide films and microcapsules include, for example, nano-reactors, biosensors, artificial cells, and drug delivery vehicles.

The design principles for incorporation of polypeptides into multilayer films were first elucidated in U.S. Patent Publication No. 2005/0069950. In brief, the suitability of a polypeptide for ELBL is related to the net charge on the polypeptide and the length of the polypeptide. A polypeptide suitable for ELBL preferably comprises one or more amino acid sequence motifs, that is, contiguous amino acid sequences having a length of about 5 to about 15 amino acid residues and having a suitable linear charge density for electrostatic deposition. A polypeptide for ELBL can be designed in different ways, for example, by joining a plurality of amino acid sequence motifs to each other, either directly, or by a linker. Polypeptides having the appropriate length and charge properties can readily be deposited to form one or more layers of a polypeptide multilayer film.

Although the basic design principles for polypeptide multilayer films have been elucidated, there nonetheless remains a need for design of polypeptide multilayer films having a desired functionality, particularly biological functionality.

SUMMARY

In one embodiment, a multilayer film comprises two or more layers of polyelectrolytes, wherein adjacent layers comprise oppositely charged polyelectrolytes. A first layer polyelectrolyte comprises a hybrid polypeptide comprising a first polypeptide segment and a second segment covalently joined by one or more non-peptidic linkages; wherein the first polypeptide segment comprises a polypeptide segment having a magnitude of net charge per residue of greater than or equal to 0.4, and a length of greater than or equal to about 12 amino acid residues. A second layer comprises a second layer polyelectrolyte comprising a polycationic material or a polyanionic material having a molecular weight of greater than 1,000 and at least 5 charges per molecule, and a charge opposite that of the first layer polypeptide.

DETAILED DESCRIPTION

Figure 2:
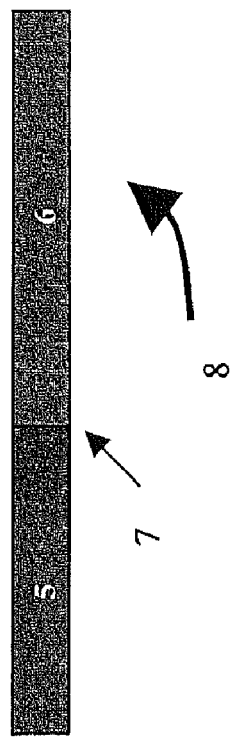
FIG. 2 illustrates an embodiment of a hybrid polypeptide.

The present invention is directed to polypeptide multilayer films comprising a hybrid polypeptide, the hybrid polypeptide comprising a first polypeptide segment and a second segment, the two segments being covalently joined by one or more non-peptidic linkages. The first segment comprises a polypeptide having a magnitude of net charge per residue of greater than or equal to 0.4, and a length of greater than or equal to about 12 amino acid residues. The first segment, thus, is a designed polypeptide segment comprising one or more amino acid sequence motifs. The second segment comprises a polypeptide or a nonpolypeptide polyelectrolyte. In one embodiment, for example, when the second segment comprises a nonpolypeptide electrolyte, both the first segment and the second segment have a net charge of the same sign at neutral pH; that is, both segments are positively charged or both segments are negatively charged. FIG. 2 illustrates a hybrid polypeptide (8) comprising a first polypeptide segment (5) and a second segment (6) joined by a non-peptidic linker (7).

As used herein, "layer" means a thickness increment, e.g., on a substrate for film formation, following an adsorption step. "Multilayer" means multiple (i.e., two or more) thickness increments. A "polyelectrolyte multilayer film" is a film comprising one or more thickness increments of polyelectrolytes. After deposition, the layers of a multilayer film may not remain as discrete layers. In fact, it is possible that there is significant intermingling of species, particularly at the interfaces of the thickness increments.

As used herein, "hybrid polypeptide" means a molecule comprising a first polypeptide segment and a second segment covalently joined by one or more non-peptidic linkages. The first and second segments may or may not have the same sign of net charge at neutral pH. In one embodiment, when the second segment comprises a second polypeptide segment, the hybrid polypeptide comprises 15 or more amino acid residues. While there is no absolute upper limit on the length of the hybrid polypeptide, in general, hybrid polypeptides suitable for ELBL deposition have a practical upper length limit of 1,000 residues. In one embodiment, the hybrid polypeptide is non-branched, that is, the hybrid polypeptide is formed from constituent polypolypeptides by way of chain termini only, the chain termini being amino- or N-termini and carboxyl- or C-termini, or chemical modifications of these termini. A branched polypeptide, by contrast, comprises a backbone peptide having an N-terminus and a C-terminus or chemical modifications thereof, and one or more peptide branches from side chains of amino acid residues in the backbone peptide. The key distinction between these two cases is the site of attachment of a polypeptide, e.g., B, to another polypeptide, e.g. A. In the non-branched case, B is attached to A at a chain terminus of A. In the branched case, B is attached to backbone peptide A by way of a side chain of A.

The term "non-peptidic linkage" means a chemical linkage other than a peptide bond. A peptide bond is a CO—NH bond formed between two molecules (e.g., amino acids) when the carboxyl group of one molecule reacts with the amino group of the other molecule, releasing a molecule of water ($H_2O$).

The term "polyelectrolyte" includes polycationic and polyanionic materials. When employed as an independent layer of a multilayer film, polyelectrolytes have a molecular weight of greater than 1,000 and at least 5 charges per molecule. When employed as a second segment of a hybrid polypeptide, smaller polyelectrolytes may be employed. Suitable polycationic materials include, for example, polyamines. Polyamines include, for example, a polypeptide, polyvinyl amine, poly(aminostyrene), poly(aminoacrylate), poly(N-methyl aminoacrylate), poly(N-ethylaminoacrylate), poly(N,N-dimethyl aminoacrylate), poly(N,N-diethylaminoacrylate), poly(aminomethacrylate), poly(N-methyl amino-methacrylate), poly(N-ethyl aminomethacrylate), poly(N,N-dimethyl aminomethacrylate), poly(N,N-diethyl aminomethacrylate), poly(ethyleneimine), poly(diallyl dimethylammonium chloride), poly(N,N,N-trimethylaminoacrylate chloride), poly(methyacrylamidopropyltrimethyl ammonium chloride), chitosan and combinations comprising one or more of the foregoing polycationic materials. Suitable polyanionic materials include, for example, a polypeptide, a nucleic acid, alginate, carrageenan, furcellaran, pectin, xanthan, hyaluronic acid, heparin, heparan sulfate, chondroitin sulfate, dermatan sulfate, dextran sulfate, poly(meth)acrylic acid, oxidized cellulose, carboxymethyl cellulose, acidic polysaccharides, and croscarmelose, synthetic polymers and copolymers containing pendant carboxyl groups, and combinations comprising one or more of the foregoing polyanionic materials.

"Amino acid" means a building block of a polypeptide. As used herein, "amino acid" includes the 20 common naturally occurring L-amino acids, all other natural amino acids, all non-natural amino acids, and all amino acid mimics, e.g., peptoids.

"Naturally occurring amino acids" means the 20 common naturally occurring L-amino acids, that is, glycine, alanine, valine, leucine, isoleucine, serine, threonine, cysteine, methionine, aspartic acid, asparagine, glutamic acid, glutamine, arginine, lysine, histidine, phenylalanine, tyrosine, tryptophan, and proline.

"Non-natural amino acid" means an amino acid other than any of the common naturally occurring L-amino acids. A non-natural amino acid can have either L- or D-stereochemistry.

"Peptoid," or N-substituted glycine, means an analog of the corresponding amino acid monomer, with the same side chain as the corresponding amino acid but with the side chain appended to the nitrogen atom of the amino group rather than to the α-carbons of the residue. Consequently, the chemical linkages between monomers in a polypeptoid are not polypeptide bonds, which can be useful for limiting proteolytic digestion.

"Amino acid sequence" and "sequence" mean a contiguous length of polypeptide chain that is at least two amino acid residues long.

"Residue" means a subunit in a polymer of any length. In a polypeptide, an amino acid residue is the residue of the amino acid monomer which has been added to the polymer. Polypeptide synthesis involves dehydration, that is, the loss of a single water molecule on addition of the amino acid monomer to a polypeptide chain.

"Amino acid sequence motif" means a contiguous amino acid sequence comprising n residues, wherein n is 5 to 15. In one embodiment, the magnitude of the net charge per residue of an amino acid sequence motif is greater than or equal to 0.4. In another embodiment, the magnitude of the net charge per residue of an amino acid sequence motif is greater than or equal to 0.5. As used herein, the magnitude of the net charge refers to the absolute value of the net charge, that is, the net charge can be positive of negative.

"Designed polypeptide segment" means a polypeptide segment, wherein the polypeptide segment is at least 12 amino acids in length and the ratio of the number of charged residues of the same polarity minus the number of residues of the opposite polarity to the total number of residues in the polypeptide segment is greater than or equal to 0.4 at pH 7.0. In other words, the magnitude of the net charge per residue of the polypeptide segment is greater than or equal to 0.4. In one embodiment, the ratio of the number of charged residues of the same polarity minus the number of residues of the opposite polarity to the total number of residues in the polypeptide segment is greater than or equal to 0.5 at pH 7.0. In other words, the magnitude of the net charge per residue of the polypeptide segment is greater than or equal to 0.5.

"Designed polypeptide" means a polypeptide comprising one or more amino acid sequence motifs, wherein the polypeptide is at least 15 amino acids in length and the ratio of the number of charged residues of the same polarity minus the number of residues of the opposite polarity to the total number of residues in the polypeptide is greater than or equal to 0.4 at pH 7.0. In other words, the magnitude of the net charge per residue of the polypeptide is greater than or equal to 0.4. In one embodiment, the ratio of the number of charged residues of the same polarity minus the number of residues of the opposite polarity to the total number of residues in the polypeptide is greater than or equal to 0.5 at pH 7.0. In other words, the magnitude of the net charge per residue of the polypeptide is greater than or equal to 0.5. While there is no absolute upper limit on the length of the designed polypeptide, in general, designed polypeptides suitable for ELBL deposition have a practical upper length limit of 1,000 residues.

"Primary structure" means the contiguous linear sequence of amino acids in a polypeptide chain, and "secondary structure" means the more or less regular types of structure in a polypeptide chain stabilized by non-covalent interactions, usually hydrogen bonds. Examples of secondary structure include α-helix, β-sheet, and β-turn.

"Polypeptide multilayer film" means a film comprising one or more polypeptides such as the hybrid polypeptides defined above. For example, a polypeptide multilayer film comprises a first layer comprising a hybrid polypeptide and a second layer comprising a polyelectrolyte have a net charge of opposite polarity to the designed polypeptide. For example, if the first layer has a net positive charge, the second layer has a net negative charge; and if the first layer has a net negative charge, the second layer has a net positive charge. The second layer comprises another hybrid polypeptide or another polyelectrolyte.

"Substrate" means a solid material with a suitable surface for adsorption of polyelectrolytes from aqueous solution. The surface of a substrate can have essentially any shape, for example, planar, spherical, rod-shaped, and the like. Substrate surface are regular or irregular. A substrate can be a crystal. A substrate optionally includes bioactive molecules. Substrates range in size from the nanoscale to the macroscale. Moreover, a substrate optionally comprises several small sub-particles. A substrate can be made of organic material, inorganic material, bioactive material, or a combination thereof. Nonlimiting examples of substrates include silicon wafers; charged colloidal particles, e.g., microparticles of $CaCO_3$ or of melamine formaldehyde; protein crystals; nucleic acid crystals; biological cells such as erythrocytes, hepatocytes, bacterial cells, or yeast cells; organic polymer lattices, e.g., polystyrene or styrene copolymer lattices; liposomes; organelles; and viruses. In one embodiment, a substrate is a medical device such as an artificial pacemaker, a cochlear implant, or a stent.

When a substrate is disintegrated or otherwise removed during or after film formation, it is called "a template" (for film formation). Template particles can be dissolved in appropriate solvents or removed by thermal treatment. If, for example, partially cross-linked melamine formaldehyde template particles are used, the template can be disintegrated by mild chemical methods, e.g., in DMSO, or by a change in pH value. After dissolution of the template particles, hollow multilayer shells remain which are composed of alternating polyelectrolyte layers.

A "microcapsule" is a polyelectrolyte film in the form of a hollow shell or a coating surrounding a core. The core comprises a variety of different encapsulants, such as, a protein, a drug, or a combination thereof, in liquid or crystalline form, for example.

"Bioactive molecule" means a molecule, macromolecule, or macromolecular assembly having a biological effect. The specific biological effect can be measured in a suitable assay and normalizing per unit weight or per molecule of the bioactive molecule. A bioactive molecule can be encapsulated, retained behind, or encapsulated within a polyelectrolyte film. Nonlimiting examples of a bioactive molecule are a drug, a crystal of a drug, a protein, a functional fragment of a protein, a complex of proteins, a lipoprotein, an oligopeptide, an oligonucleotide, a nucleic acid, a ribosome, an active therapeutic agent, a phospholipid, a polysaccharide, a lipopolysaccharide. As used herein, "bioactive molecule" further encompasses biologically active structures, such as, for example, a functional membrane fragment, a membrane structure, a virus, a pathogen, a cell, an aggregate of cells, and an organelle. Examples of a protein that can be encapsulated or retained behind a polypeptide film are hemoglobin; enzymes, such as for example glucose oxidase, urease, lysozyme and the like; extracellular matrix proteins, for example, fibronectin, laminin, vitronectin and collagen; and an antibody. Examples of a cell that can be encapsulated or retained behind a polyelectrolyte film is a transplanted islet cell, a eukaryotic cell, a bacterial cell, a plant cell, and a yeast cell.

"Biocompatible" means causing no substantial adverse health effect upon oral ingestion, topical application, transdermal application, subcutaneous injection, intramuscular injection, inhalation, implantation, or intravenous injection. For example, biocompatible films include those that do not cause a substantial immune response when in contact with the immune system of, for example, a human being.

"Immune response" means the response of the cellular or humoral immune system to the presence of a substance anywhere in the body. An immune response can be characterized in a number of ways, for example, by an increase in the bloodstream of the number of antibodies that recognize a certain antigen. Antibodies are proteins secreted by B cells, and an antigen is an entity that elicits an immune response. The human body fights infection and inhibits reinfection by increasing the number of antibodies in the bloodstream and elsewhere. The specific immune response depends somewhat on the individual, though general patterns of response are the norm.

"Epitope" means the structure or sequence of a protein that is recognized by an antibody. Ordinarily an epitope will be on the surface of a protein. A "continuous epitope" is one that involves several contiguous amino acid residues, not one that involves amino acid residues that happen to be in contact or in the limited region of space in a folded protein.

The present invention is directed to polypeptide multilayer films, wherein the films comprise a hybrid polypeptide. Other layers comprise designed polypeptides or other polycations or polyanions.

The design principles for polypeptides and polypeptide segments suitable for electrostatic layer-by-layer deposition are elucidated in U.S. Patent Publication No. 2005/0069950, incorporated herein by reference. Briefly, the primary design concerns are the length and charge of the polypeptide. Electrostatics is the most important design concern because it is the basis of ELBL. Without suitable charge properties, a polypeptide will not be substantially soluble in aqueous solution at pH 4 to 10 and cannot readily be used for the fabrication of a multilayer film by ELBL. Other design concerns include the physical structure of the polypeptides, the physical stability of the films formed from the polypeptides, and the biocompatibility and bioactivity of the films and the constituent polypeptides.

As defined above, a designed polypeptide means a polypeptide comprising one or more amino acid sequence motifs, wherein the polypeptide is at least 15 amino acid residues in length and the magnitude of the net charge per residue of the polypeptide is greater than or equal to 0.4 at pH 7.0. A designed polypeptide segment means a polypeptide segment, wherein the polypeptide is at least 12 amino acid residues in length and the magnitude of the net charge per residue of the polypeptide is greater than or equal to 0.4 at pH 7.0. Polypeptide segments generally comprise amino acid sequence motifs. "Amino acid sequence motif" means a contiguous amino acid sequence comprising n amino acid residues, wherein n is 5 to 15. Positively-charged (basic) naturally-occurring amino acids at pH 7.0 are Arg, His, and Lys. Negatively-charged (acidic) naturally-occurring amino acid residues at pH 7.0 are Glu and Asp. An amino acid sequence motif comprising a mixture of amino acid residues of opposite charge can be employed so long as the overall ratio of charge meets the specified criteria. In one embodiment, a designed polypeptide is not a homopolymer.

In one exemplary embodiment, the amino acid sequence motif comprises 7 amino acid residues. Four charged amino acids is a suitable minimum for a motif size of 7, because fewer than 4 charges yields decreased polypeptide solubility and decreased control over ELBL. Further, regarding biocompatibility, each identified amino acid sequence motif in genomic data is long enough at 7 amino acid residues to constitute a continuous epitope, but not so long as to correspond substantially to residues both on the surface of a protein and in its interior. Thus, the charge and length of the amino acid sequence motif help to ensure that an amino acid sequence motif identified in genomic data is likely to occur on the surface of the folded protein from which the sequence motif is derived. In contrast, a very short motif could appear to the body to be a random sequence, or one not specifically "self;" and therefore elicit an immune response.

In some cases, a design concern regarding amino acid sequence motifs, designed polypeptides, hybrid polypeptides and polypeptide segments is their propensity to form secondary structures, notably α-helix or β-sheet. In some embodiments, it is desirable to be able to control, e.g., minimize, secondary structure formation by the polypeptides in an aqueous medium in order to maximize control over thin film layer formation. First, it is preferred that sequence motifs be relatively short, that is about 5 to about 15 amino acid residues, because long motifs are more likely to adopt a stable three-dimensional structure in solution. Second, a linker, such as a glycine or proline residue, covalently joined between successive amino acid sequence motifs in a designed polypeptide will reduce the propensity of the polypeptide to adopt secondary structure in solution. Glycine, for example, has a very low α-helix propensity and a very low β-sheet propensity, making it energetically very unfavorable for a glycine and its neighboring amino acids to form regular secondary structure in aqueous solution. Third, the α-helix and β-sheet propensity of the designed polypeptides themselves can be minimized by selecting amino acid sequence motifs for which the summed α-helix propensity is less than 7.5 and the summed β-sheet propensity is less than 8. "Summed" propensity means the sum of the α-helix or β-sheet propensities of all amino acids in a motif. Amino acid sequence motifs having a somewhat higher summed α-helix propensity and/or summed β-sheet propensity are suitable for ELBL, particularly when joined by linkers such as Gly or Pro. In certain applications, the propensity of a polypeptide to form secondary structure can be relatively high as a specific design feature of thin film fabrication. The secondary structure propensities for all 20 naturally occurring amino acids can be calculated using the method of Chou and Fasman (see P. Chou and G. Fasman, *Biochemistry*, 13:211 (1974), which is incorporated by reference herein in its entirety).

Another design concern is control of the stability of polypeptide ELBL films. Ionic bonds, hydrogen bonds, van der Waals interactions, and hydrophobic interactions contribute to the stability of multilayer films. In addition, covalent disulfide bonds formed between sulfhydryl-containing amino acids in the polypeptides and/or polypeptide segments within the same layer or in adjacent layers can increase structural strength. Sulfhydryl-containing amino acids include cysteine and homocysteine. In addition, a sulfhydryl can be added to β-amino acids such as D,L-β-amino-β-cyclohexyl propionic acid; D,L-3-aminobutanoic acid; or 5-(methylthio)-3-aminopentanoic acid. Sulfhydryl-containing amino acids can be used to "lock" (bond together) and "unlock" layers of a multilayer polypeptide film by a change in oxidation potential. Also, the incorporation of a sulfhydryl-containing amino acid in a sequence motif of a designed or hybrid polypeptide enables the use of relatively short peptides in thin film fabrication, by virtue of intermolecular disulfide bond formation. Amino acid sequence motifs containing sulfhydryl-containing amino acids may be selected from a library of motifs identified using the methods described below, or designed de novo.

In one embodiment, the designed or hybrid sulfhydryl-containing polypeptides are assembled by ELBL in the presence of a reducing agent to prevent premature disulfide bond formation. Following film assembly, the reducing agent is removed and an oxidizing agent is added. In the presence of the oxidizing agent disulfide bonds form between sulfhydryls groups, thereby "locking" together the polypeptides within layers and between layers where thiol groups are present. Suitable reducing agents include dithiothreitol ("DTT"), 2-mercaptoethanol (2-ME), reduced glutathione, tris(2-carboxyethyl)phosphine hydrochloride (TCEP), and combinations of more than one of these chemicals. Suitable oxidizing agents include oxidized glutathione, tert-butylhydroperoxide (t-BHP), thimerosal, diamide, 5,5'-dithio-bis-(2-nitro-benzoic acid) (DTNB), 4,4'-dithiodipyridine, sodium bromate, hydrogen peroxide, sodium tetrathionate, porphyrindin, sodium orthoiodosobenzoate, and combinations of more than one of these chemicals.

Biocompatibility is a design concern in biomedical applications. In such applications, genomic or proteomic information is used as a basis for polymer design to yield, ideally, "immune inert" polypeptides. The approach will be particularly useful if the fabricated or coated object will make contact with circulating blood. Because the amino acid sequence motifs are highly polar, they typically occur on the surface of the native folded form of the protein from which they are derived. The "surface" is that part of a folded protein that is in contact with the solvent or inaccessible to the solvent solely because of the granular nature of water. Amino acid sequence motifs identified in blood proteins are effectively always in contact with cells and molecules of the immune system while the protein is in the blood. Therefore, polypeptides derived from the surface of folded blood proteins are less likely to be immunogenic than sequences selected at random. Designed and hybrid polypeptides will generally be biocompatible, but the extent of immune response or any other type of biological response may well depend on specific details of a sequence motif.

Bioactivity can be incorporated into a film, coating or microcapsule by a number of methods. Alternatively, bioactivity may be associated with another bioactive molecule encapsulated or coated by the polypeptide thin film. In one embodiment, the template comprises a bioactive molecule such as a protein crystal.

The bioactive molecule can be a protein, a functional fragment of a protein, a functional fragment of a protein that is not part of a designed polypeptide or a hybrid polypeptide, a complex of proteins, an oligopeptide, an oligonucleotide, a nucleic acid, a ribosome, an active therapeutic agent, a phospholipid, a polysaccharide, a lipopolysaccharide, a functional membrane fragment, a membrane structure, a virus, a pathogen, a cell, an aggregate of cells, an organelle, a lipid, a carbohydrate, a pharmaceutical, or an antimicrobial agent. The bioactive molecule can be in the form of a well-ordered or amorphous crystal. The protein can be an enzyme or an antibody. The substrate can comprise the bioactive molecule. In one embodiment, the substrate has a bioactive molecule disposed on its surface prior to deposition of layers of oppositely charged polypeptides. In another embodiment, the substrate is a crystal comprising the bioactive molecule.

In one embodiment, amino acid sequence motifs are designed de novo. In other embodiments, amino acid sequence motifs are selected from the genomic or proteomic information of a specific organism, such as the human genome.

Amino acid sequence motifs can be identified in known polypeptide sequences or designed de novo. A method of identifying a first amino acid sequence motif in a polypeptide comprises selecting a starter amino acid residue in the polypeptide; examining an amino acid sequence comprising the starter amino acid residue and the following n−1 amino acid residues in the polypeptide for occurrences of positive and negative charges, wherein n is 5 to 15; determining the 5-15 amino acid residues as an amino acid sequence motif if the net charge of the side chains of the 5-15 amino acid residues at pH 7 is greater than or equal to 0.4*n; or discarding the sequence if the net charge of the side chains of the 5-15 amino acid residues at pH 7 is less than 0.4*n.

In one embodiment, the process of searching protein sequence data for a negatively charged amino acid sequence motif of length n comprising only amino acids that are neutral or negatively charged is described as follows. First, a first amino acid residue is selected in a protein sequence. Second, this amino acid residue and the following n−1 amino acid residues are examined for occurrences of arginine (Arg), histidine (His), or lysine (Lys) (the three naturally occurring amino acids that may be positively charged at neutral pH), where n is 5 to 15. Third, if one or more Arg, His, or Lys residues is found in these n amino acid residues, the process is begun anew at a second amino acid residue. If, however, no Arg, His, or Lys is found in these n residues, the n residues are examined to determine the number of occurrences of glutamate (Glu) and/or aspartate (Asp) (the two negatively charged amino acids at neutral pH). Fourth, if there are at least 0.4*n occurrences of Glu and/or Asp in the n residues, the sequence is cataloged as a negatively charged amino acid sequence motif. If, however, fewer than 0.4*n occurrences of negatively charged amino acid residues are found, the sequence beginning with the first amino acid residue is discarded and the process is begun anew, for example, at a second amino acid residue immediately adjacent to the first amino acid residue. After cataloging a motif, the process can begin anew at a second amino acid residue.

The process for identifying a positively charged sequence motif is analogous to searching protein sequence data for an n residue-long amino acid sequence comprising only amino acid residues that are neutral or positively charged, and for which the magnitude of the net charge of the amino acid residue side chains at neutral pH is greater than or equal to 0.4*n.

Also analogous is the process for identifying a negatively charged amino acid sequence motif or a positively charged amino acid sequence motif of length n, allowing both positively and negatively charged amino acid residues in the motif. For example, the procedure for identifying a positively charged amino acid sequence motif of length n would be to select a first amino acid residue in a polypeptide. Next, examine this amino acid residue and the following n−1 amino acid residues for occurrences of residues that are positively or negatively charged at pH 7. Determine the net charge of the n amino acid residue side chains. If the absolute value of the net charge is less than 0.4*n, then the sequence is discarded and a new search is begun at another amino acid, while if the absolute value of the net charge is greater than or equal to 0.4*n, then the sequence is an amino acid sequence motif. The motif will be positive if net charge is greater than zero and negative if the net charge is less than zero.

De novo design of amino acid sequence motifs as presently defined follows essentially similar rules, except that the sequences are not limited to those found in nature. A length of motif n and a desired sign and magnitude of net charge are chosen. Then, n amino acids are selected for the amino acid sequence motif that result in the desired sign and magnitude of charge, so that the absolute value of the net charge of the n amino acids is greater than or equal to 0.4*n. A potential advantage of de novo design of an amino acid sequence motif is that the practitioner can select from among all amino acids (the 20 naturally occurring ones and all non-natural amino acids) to achieve the desired net charge, rather than being limited to the amino acids found in a particular known protein sequence. The larger pool of amino acids enlarges the potential range of physical, chemical and/or biological characteristics that can be selected in designing the sequence of the motif compared to identification of an amino acid sequence motif in a genomic sequence.

A designed or hybrid polypeptide as presently defined will comprise one or more amino acid sequence motifs. The same motif may be repeated, or different motifs may be joined in designing a polypeptide for ELBL. In one embodiment, the amino acid sequence motifs are covalently joined with no intervening sequence. In another embodiment, a designed or hybrid polypeptide comprises two or more amino acid sequence motifs covalently joined by a linker. The linker can be amino acid based, e.g., one or more amino acid residues such as glycine or proline, or it can be any other compound suitable for covalently linking two amino acid sequence motifs. In one embodiment, a linker comprises 1-4 amino acid residues, for example, 1-4 glycine and/or proline resides. The linker comprises a suitable length or composition so that the designed polypeptide is maintained at a magnitude of net charge per residue that is greater than or equal to 0.4.

In one embodiment, a designed or hybrid polypeptide is greater than or equal to 15 residues (e.g., amino acid residues) long. In other embodiments, a designed polypeptide is greater than 18, 20, 25, 30, 32 or 35 residues long. 1,000 residues is a practical upper bound on polypeptide length.

Once amino acid sequence motifs have been selected or designed de novo, a designed polypeptide or polypeptide segment with amino acid-based linkers is synthesized using methods well known in the art, such as solid phase synthesis and F-moc chemistry, or heterologous expression in bacteria following gene cloning and transformation. Designed polypeptides and polypeptide segments may be synthesized by a polypeptide synthesis company, for example, Global Polypeptide (Ft Collins, Colo.), produced in the laboratory using a polypeptide synthesizer, or produced by recombinant DNA methods. Any development of novel methods of polypeptide synthesis could enhance the production of peptides but would not fundamentally change polypeptide design as described herein.

Figure 1:
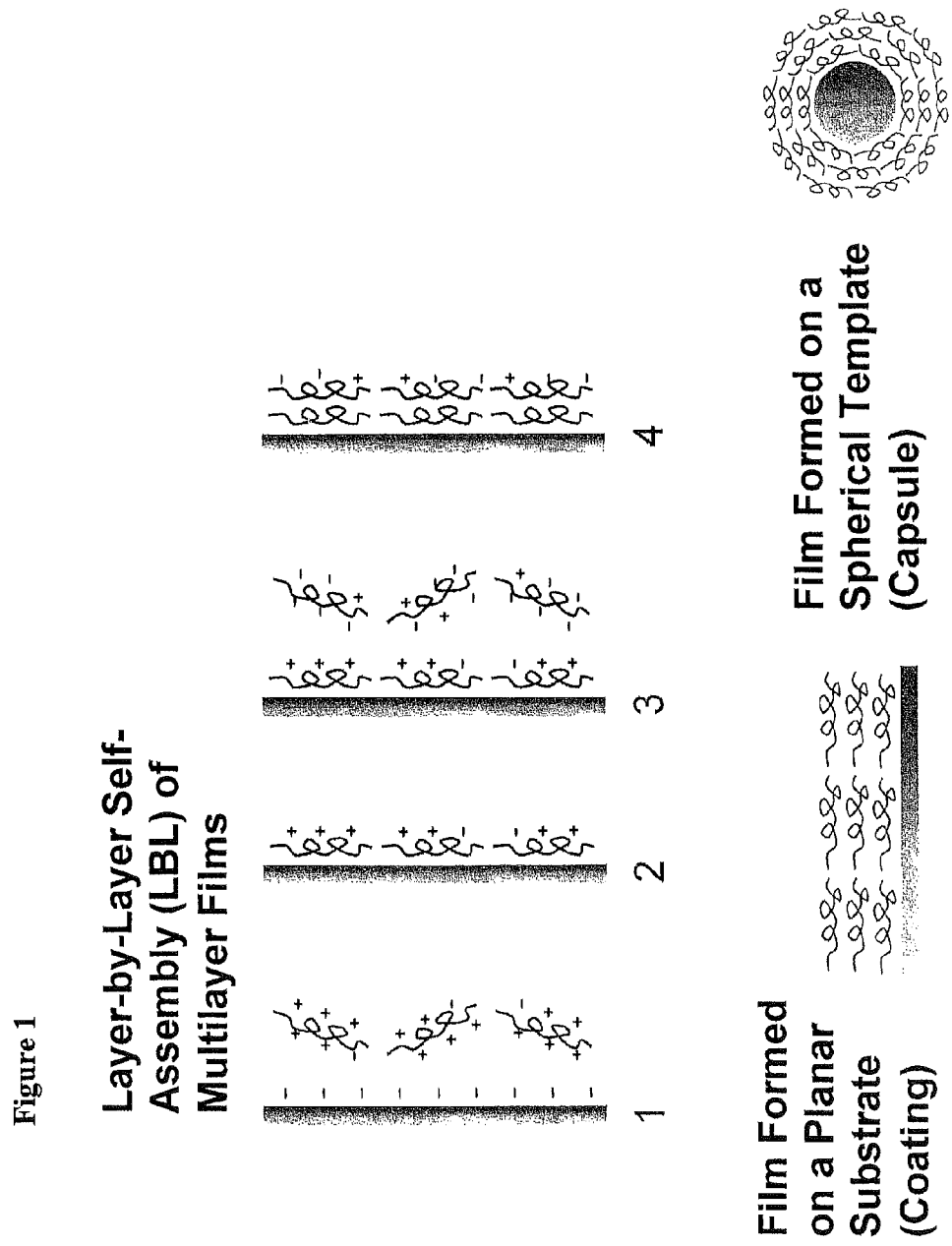
FIG. 1 shows a schematic of the assembly of oppositely charged polypeptides.

A method of making a polyelectrolyte multilayer film comprises depositing a plurality of layers of oppositely charged polyelectrolytes on a substrate. Successively deposited polyelectrolytes have opposite net charges. FIG. 1 is a schematic illustrating ELBL deposition. In one embodiment, deposition of a polyelectrolyte such as a hybrid polypeptide comprises exposing the substrate to an aqueous solution comprising a hybrid polypeptide (or other polyelectrolyte) at a pH at which it has a suitable net charge for ELBL. In other embodiments, the deposition of a hybrid polypeptide or other polyelectrolyte on the substrate is achieved by sequential spraying of solutions of oppositely charged polyelectrolytes. In yet other embodiments, deposition on the substrate is by simultaneous spraying of solutions of oppositely charged polyelectrolytes.

In the ELBL method of forming a multilayer film, the opposing charges of the adjacent layers provide the driving force for assembly. It is not critical that polyelectrolytes in opposing layers have the same net linear charge density, only that opposing layers have opposite charges. One standard film assembly procedure for deposition includes forming aqueous solutions of the polyelectrolytes at a pH at which they are ionized (i.e., pH 4-10), providing a substrate bearing a surface charge, and alternating immersion of the substrate into the charged polyelectrolyte solutions. The substrate is optionally washed in between deposition of alternating layers.

The concentration of polyelectrolyte suitable for deposition of the polyelectrolyte can readily be determined by one of ordinary skill in the art. An exemplary concentration is 0.1 to 10 mg/mL. Typically, the thickness of the layer produced is substantially independent of the solution concentration of the polyion during deposition in the stated range. For typical non-polypeptide polyelectrolytes such as poly(acrylic acid) and poly(allylamine hydrochloride), layer thicknesses are about 3 to about 5 Å, depending on the ionic strength of solution. Short polyelectrolytes often form thinner layers than long polyelectrolytes. Regarding film thickness, polyelectrolyte film thickness depends on humidity as well as the number of layers and composition of the film. For example, PLL/PLGA films 50 nm thick shrink to 1.6 nm upon drying with nitrogen. In general, films of 1 nm to 100 nm or more in thickness can be formed depending on the hydration state of the film and the molecular weight of the polyelectrolytes employed in the assembly.

In addition, the number of layers required to form a stable polyelectrolyte multilayer film will depend on the polyelectrolytes in the film. For films comprising only low molecular weight polypeptide layers, a film will typically have 4 or more bilayers of oppositely charged polypeptides. For films comprising high molecular weight polyelectrolytes such as poly(acrylic acid) and poly(allylamine hydrochloride), films comprising a single bilayer of oppositely charged polyelectrolyte can be stable.

The films described herein comprise at least one polypeptide that is a hybrid polypeptide. As used herein, a hybrid polypeptide is one that comprises a first polypeptide segment and a second segment covalently joined by one or more non-peptidic linkages.

The first polypeptide segment comprises a polypeptide segment having a magnitude of net charge per residue of greater than or equal to 0.4, and a length of greater than or equal to about 12 amino acid residues. The first polypeptide segment comprises a designed polypeptide segment comprising one or more amino acid sequence motifs as defined herein. In essence, the first polypeptide segment acts as a surface adsorption region that provides suitable properties of length and charge to adsorb the hybrid polypeptide to the surface. The actual charge and length of the first polypeptide segment are at least somewhat related to the identity of the second segment, and can be determined by one of skill in the art.

The second segment comprises a polypeptide or a non-polypeptide polyelectrolyte. In one embodiment, for example, when the second segment comprises a nonpolypeptide polyelectrolyte, both the first segment and the second segment have a net charge at neutral pH of the same sign; that is, both segments are positively charged or both are negatively charged. In another embodiment, for example, when the second segment comprises a second polypeptide, the second segment is uncharged, has a net charge of the same sign as the first polypeptide segment, or has a net charge of opposite sign to the first polypeptide segment. If the second polypeptide segment has a high linear charge density, however, for example, an absolute net charge per residue greater than or equal to about 0.2, it is preferred that the first polypeptide segment and the second polypeptide segment have the same sign of charge.

In one embodiment, the hybrid polypeptide has an aqueous solubility at pH 4 to 10 of greater than 50 µg/mL. In another embodiment, the aqueous solubility of the hybrid polypeptide at pH 4 to 10 is greater than or equal to about 1 mg/mL.

As explained above, the first polypeptide segment acts as a surface adsorption region for the hybrid polypeptide. In certain embodiments, it is desirable for a hybrid polypeptide to comprise more then one surface adsorption region. Thus, the hybrid polypeptide optionally comprises a third segment wherein the third segment comprises an amino acid sequence motif. The number of surface adsorption regions in a hybrid polypeptide relative to the number and/or length of the second segments is related to the solubility requirement. For example, if the second segment is a short amino acid sequence of, for example, three amino acid residues, only one amino acid sequence motif of at least 12 amino acid residues will be required to adsorb the hybrid polypeptide onto a suitably charged surface. If, by contrast, the second segment is a soluble folded structural domain of a protein comprising, for example, 120 amino acid residues, two amino acid sequence motifs will typically be sufficient to impart enough charge for the antigenic polypeptide to be water soluble and suitable for adsorption. The motifs could be contiguous and located at the N-terminus of the domain, contiguous and located at the C-terminus of the domain, or noncontiguous with one at the N-terminus and one at the C-terminus.

The combined length of the surface adsorption regions is related more to the dissipation due to thermal energy, which must be overcome for hybrid polypeptide adsorption to occur spontaneously, than the number amino acid residues or monomer units in the second segment. Therefore, increasing the degree of polymerization of the second segment by a factor of two does not necessarily require surface adsorption regions twice as long for effective binding of the surface adsorption regions of the hybrid polypeptide. The physical basis of adsorption of a hybrid polypeptide to a surface is electrostatic attraction (and release of counterions to bulk solution), the precise mass of the second segment is of secondary importance on the length scale of nanometers, and the main "force" counteracting hybrid polypeptide adsorption is thermal energy. In view of this, one of skill in the art can readily design surface adsorption regions that are suitable for physical adsorption to a surface of the particular second segment of interest.

In one embodiment, the second segment is a polyelectrolyte optionally having the same sign of charge as the first polypeptide segment, wherein the second segment is a non-polypeptide electrolyte. In specific embodiments, when the first segment is a cationic polypeptide, the second segment comprises, for example, polyvinyl amine, poly(aminostyrene), poly(aminoacrylate), poly(N-methyl aminoacrylate), poly(N-ethylaminoacrylate), poly(N,N-dimethyl aminoacrylate), poly(N,N-diethylaminoacrylate), poly(aminomethacrylate), poly(N-methyl amino-methacrylate), poly (N-ethyl aminomethacrylate), poly(N,N-dimethyl aminomethacrylate), poly(N,N-diethyl aminomethacrylate), poly(ethyleneimine), poly(diallyl dimethylammonium chloride), poly(N,N,N-trimethylaminoacrylate chloride), poly (methyacrylamidopropyltrimethyl ammonium chloride), chitosan and combinations comprising one or more of the foregoing polycationic materials. In other embodiments, when the first segment is an anionic polypeptide, the second segment comprises, for example, a nucleic acid, alginate, carrageenan, furcellaran, pectin, xanthan, hyaluronic acid, heparin, heparan sulfate, chondroitin sulfate, dermatan sulfate, dextran sulfate, poly(meth)acrylic acid, oxidized cellulose, carboxymethyl cellulose, acidic polysaccharides, and croscarmelose, synthetic polymers and copolymers containing pendant carboxyl groups, and combinations comprising one or more of the foregoing polyanionic materials. The second segment is joined to the N-terminus, the C-terminus, or a pendant side chain of the first polypeptide segment by the non-polypeptide linker.

In one embodiment of hybrid peptides, the second segment is a polypeptide segment. The first and second polypeptide segments can be joined in a variety of different ways, depending upon the chemistry of the non-peptidic linker. For example, the N-terminus of the first polypeptide segment is joined to the C-terminus of the second polypeptide segment; the N-terminus of the first polypeptide segment is joined to the N-terminus of the second polypeptide segment; the C-terminus of the first polypeptide segment is joined to the C-terminus of the second polypeptide segment; the C-terminus of the first polypeptide segment is joined to the N-terminus of the second polypeptide segment; the C-terminus or the N-terminus of the first polypeptide segment is joined to a pendant side chain of the second polypeptide segment; or the C-terminus or the N-terminus of the second polypeptide segment is joined to a pendant side chain of the first polypeptide segment. Regardless of the point of attachment, however, the first and second segments are covalently joined by a non-peptidic linker.

In another embodiment, the hybrid polypeptide comprises a hybrid antigenic polypeptide wherein the second segment comprises an antigenic determinant region comprising 3 to about 250 amino acid residues. The term 'antigenic determinant region' includes both antigenic motifs and antigenic domains. Antigenic motifs are relatively short and therefore generally do not have a compact three-dimensional fold; nevertheless, they can comprise elements of secondary structure such as α-helices and β-sheets and exhibit specific immunogenicity. When the antigenic determinant region is an antigenic motif, it will typically comprise 3 to about 50 amino acid residues. When the antigenic determinant region is an antigenic domain, it will typically comprise about 50 to about 250 amino acid residues.

An antigenic domain is defined herein as at least a portion of a polypeptide which, when folded, creates its own hydrophobic core. A native protein, for example, may contain a plurality of structural domains, each of which acts as an independent unit of structure and function. The biological function of one domain can be completely independent of the function of another, as in the case of a catalytic domain and a binding domain in the same polypeptide chain, where the two domains do not interact with each other at all. Structural interactions between domains in a native protein are not only possible, but relatively common; in such cases the interaction between one structural domain and another structural domain can be viewed as a type of quaternary structure.

As used herein, an antigenic domain typically has a minimum of about 50 amino acid residues and a maximum of about 250 amino acid residues. In principle, any antigenic domain from a protein can be employed in an antigenic polypeptide as outlined herein so long as the antigenic polypeptide has the appropriate aqueous solubility for ELBL deposition. In one embodiment, the antigenic domain has a water solubility at pH 4 to 10 of greater than 50 µg/mL. In another embodiment, the antigenic domain has a water solubility at pH 4 to 10 of greater than or equal to 1 mg/mL.

Suitable antigenic determinant regions include viral antigens, bacterial antigens, fungal antigens, parasite antigens, tumor antigens, antigens involved in autoimmunity, and combinations comprising one or more of the foregoing antigenic determinant regions.

In one embodiment, the antigenic determinant region comprises a viral antigen. Suitable viral antigens include, but are not limited to, retroviral antigens such as HIV-1 antigens including the gene products of the gag, pol, and env genes, the Nef protein, reverse transcriptase, and other HIV components; hepatitis viral antigens such as the S, M, and L proteins of hepatitis B virus, the pre-S antigen of hepatitis B virus, and other hepatitis, e.g., hepatitis A, B, and C, viral components; influenza viral antigens such as hemagglutinin and neuraminidase and other influenza viral components; measles viral antigens such as the measles virus fusion protein and other measles virus components; rubella viral antigens such as proteins E1 and E2 and other rubella virus components; rotaviral antigens such as VP7sc and other rotaviral components; cytomegaloviral antigens such as envelope glycoprotein B and other cytomegaloviral antigen components; respiratory syncytial viral antigens such as the M2 protein and other respiratory syncytial viral antigen components; herpes simplex viral antigens such as immediate early proteins, glycoprotein D, and other herpes simplex viral antigen components; varicella zoster viral antigens such as gpI, gpII, and other varicella zoster viral antigen components; Japanese encephalitis viral antigens such as proteins E, M-E, M-E-NS 1, NS 1, NS 1-NS 2A, 80% E, and other Japanese encephalitis viral antigen components; rabies viral antigens such as rabies glycoprotein, rabies nucleoprotein and other rabies viral antigen components; and combinations comprising one or more of the foregoing antigenic determinant regions.

In another embodiment, the antigenic determinant region comprises a bacterial antigen. Suitable bacterial antigens include, but are not limited to, pertussis bacterial antigens such as pertussis toxin, filamentous hemagglutinin, pertactin, FIM2, FIM3, adenylate cyclase and other pertussis bacterial antigen components; diptheria bacterial antigens such as diptheria toxin or toxoid and other diptheria bacterial antigen components; tetanus bacterial antigens such as tetanus toxin or toxoid and other tetanus bacterial antigen components; streptococcal bacterial antigens such as M proteins and other streptococcal bacterial antigen components; gram-negative bacilli bacterial antigens; Mycobacterium tuberculosis bacterial antigens such as heat shock protein 65 (HSP65), the 30 kDa major secreted protein, antigen 85A and other mycobacterial antigen components; Helicobacter pylori bacterial antigen components; pneumococcal bacterial antigens such as pneumolysin, and other pneumococcal bacterial antigen components; haemophilus influenza bacterial antigens; anthrax bacterial antigens such as anthrax protective antigen and other anthrax bacterial antigen components; rickettsiae bacterial antigens such as romps and other rickettsiae bacterial antigen components; and combinations comprising one or more of the foregoing antigenic determinant regions.

In another embodiment, the antigenic determinant region comprises a fungal antigen. Suitable fungal antigens include, but are not limited to, candida fungal antigen components; histoplasma fungal antigens such as heat shock protein 60 (HSP60) and other histoplasma fungal antigen components; cryptococcal fungal antigens such as capsular polysaccharides and other cryptococcal fungal antigen components; coccidiodes fungal antigens such as spherule antigens and other coccidiodes fungal antigen components, and tinea fungal antigens such as trichophytin and other coccidiodes fungal antigen components; and combinations comprising one or more of the foregoing antigenic determinant regions.

In another embodiment, the antigenic determinant region comprises a parasite antigen. Suitable protozoal and other parasitic antigens include, but are not limited to, plasmodium falciparum antigens such as merozoite surface antigens, sporozoite surface antigens, circumsporozoite antigens, gametocyte/gamete surface antigens, blood-stage antigen pf 1 55/RESA and other plasmodial antigen components; toxoplasma antigens such as SAG-1, p30 and other toxoplasma antigen components; schistosomae antigens such as glutathione-S-transferase, paramyosin, and other schistosomal antigen components; leishmania major and other leishmaniae antigens such as gp63, lipophosphoglycan and its associated protein and other leishmanial antigen components; and trypanosoma cruzi antigens such as the 75-77 kDa antigen, the 56 kDa antigen and other trypanosomal antigen components; and combinations comprising one or more of the foregoing parasite antigens.

In one embodiment, the antigenic determinant region comprises a tumor antigen. Suitable tumor antigens include, but are not limited to, prostate specific antigen (PSA), telomerase; multidrug resistance proteins such as P-glycoprotein; MAGE-1, alpha fetoprotein, carcinoembryonic antigen, mutant p53, papillomavirus antigens, gangliosides or other carbohydrate-containing components of melanoma or other tumor cells; and combinations comprising one or more of the foregoing tumor antigens. It is contemplated that antigens from any type of tumor cell can be used in the compositions and methods described herein.

In another embodiment, the antigenic determinant region comprises an antigen involved in autoimmunity. Suitable antigens which have been shown to be involved in autoimmunity include, but are not limited to, myelin basic protein, myelin oligodendrocyte glycoprotein and proteolipid protein of multiple sclerosis and CII collagen protein of rheumatoid arthritis; and combinations comprising one or more of the foregoing antigenic determinant regions.

Knowledge of antigenic determinants or epitopes for antigens of the pathogen of the target disease can be a useful starting point for the development of synthetic polypeptide vaccines. The more that is known about a pathogen, its mechanisms of action, and how the immune system responds to infection, the better the odds of preparing a successful vaccine. Complete determination of the structure of the genome of a pathogen is a routine and rapid procedure which can aid in the determination of antigenic determinant sites for know pathogens.

Methods and techniques for determining the location and composition of an antigenic determinant or epitope for a specific antibody are well known in the art. These techniques can be used to identify and/or characterize epitopes for use as antigenic determinant regions. In one embodiment, mapping/characterization methods of an epitope for an antigen specific antibody can be determined by epitope "foot-printing" using chemical modification of the exposed amines/carboxyls in the antigenic protein. One example of such a foot-printing technique is the use of HXMS (hydrogen-deuterium exchange detected by mass spectrometry) wherein a hydrogen/deuterium exchange of receptor and ligand protein amide protons, binding, and back exchange occurs, wherein the backbone amide groups participating in protein binding are protected from back exchange and therefore will remain deuterated. Relevant regions may be identified at this point by peptic proteolysis, fast microbore high-performance liquid chromatography separation, and/or electrospray ionization mass spectrometry.

In another embodiment, a suitable epitope identification technique is nuclear magnetic resonance (NMR) epitope mapping, where the position of the signals in two-dimensional NMR spectra of the free antigen and the antigen complexed with the antigen binding polypeptide, such as an antibody, are compared. The antigen is selectively isotopically labeled with 15N so that only signals corresponding to the antigen and no signals from the antigen binding polypeptide are seen in the NMR-spectrum. Antigen signals originating from amino acids involved in the interaction with the antigen binding polypeptide typically will shift position in the spectra of the complex compared to the spectra of the free antigen, and the amino acids involved in the binding may be identified that way.

In another embodiment, epitope mapping/characterization may be done by polypeptide scanning. In this approach, a series of overlapping peptides spanning the full-length of the polypeptide chain of an antigen are prepared and tested individually with regard to immunogenicity. The antibody titer of the corresponding polypeptide antigen is determined by a standard method, e.g., enzyme-linked immunosorbent assay. The various peptides can then be ranked with regard to immunogenicity, providing an empirical basis for selection of polypeptide design for vaccine development.

In another embodiment, protease digestion techniques may are useful in the context of epitope mapping and identification. Antigenic determinant-relevant regions/sequences are determined, for example, by protease digestion, e.g., by using trypsin in a ratio of about 1:50 to antigenic protein overnight (O/N) digestion at 37° C. and pH 7-8, followed by mass spectrometry (MS) analysis for polypeptide identification. The peptides protected from trypsin cleavage by the antigenic protein are subsequently identified by comparison of samples subjected to trypsin digestion and samples incubated with CD38BP and then subjected to digestion by trypsin, for example (thereby revealing a foot print for the binder). Other suitable enzymes include chymotrypsin, pepsin, and the like. Moreover, protease digestion provides a quick method for determining the location of a potential antigenic determinant sequence within a known antigenic protein using a known antibody.

In one embodiment, a multilayer film comprises a plurality of antigenic determinant regions, either on the same or different antigenic polypeptides. The plurality of antigenic determinants may be from the same or different infectious agents. In one embodiment, the multilayer film comprises a plurality of unique antigenic polypeptides. In another embodiment, the multilayer film comprises a plurality of immunogenic peptides comprising multiple antigenic determinant regions within each polypeptide. In another embodiment, the polypeptide is a conjugated polypeptide comprising an antigenic polypeptide mixture conjugated to a lipid moiety, or conjugated to a carrier protein moiety. An advantage of these multilayer films is that multiple antigenic determinants or multiple conformations of a single linear antigenic determinant can be present in a single synthetic vaccine particle. Such compositions with multiple antigenic determinants can potentially yield antibodies against multiple epitopes, increasing the odds that at least some of the antibodies generated by the immune system of the organism will neutralize the pathogen or target specific antigens on cancer cells, for example.

In another embodiment, a hybrid polypeptide comprises a hybrid composite polypeptide, wherein the first polypeptide segment is covalently linked to a second polypeptide segment comprising one or more functional regions, wherein the covalent linkage is a non-peptidic linkage. In one embodiment, the hybrid composite polypeptide has a solubility in aqueous solution at pH 4 to 10 of greater than 50 µg/mL. In one embodiment, the first polypeptide segment and the one or more functional regions (i.e., the second segment) have the same polarity. In another embodiment, the solubility of the first layer hybrid composite polypeptide at pH 4 to 10 is greater than or equal to about 1 mg/mL. The solubility is a practical limitation to facilitate deposition of the polypeptides from aqueous solution. A practical upper limit on the degree of polymerization of a hybrid composite polypeptide is about 1,000 residues. It is conceivable, however, that longer hybrid composite polypeptides could be realized by an appropriate method of synthesis.

Figure 3:
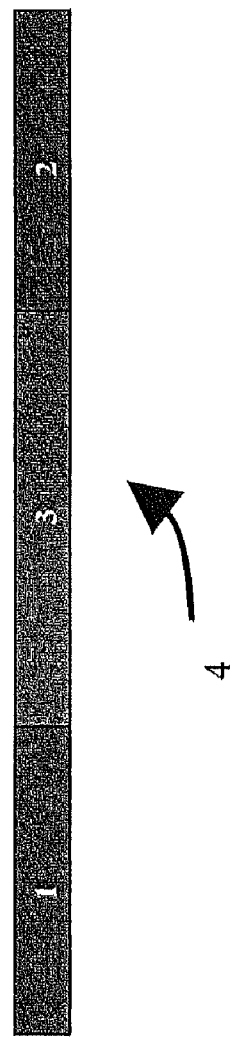
FIG. 3 illustrates an embodiment of a hybrid composite polypeptide.

In one embodiment, a hybrid composite polypeptide comprises a first polypeptide segment and a second segment comprising a functional domain. In another embodiment, a hybrid composite polypeptide (4) comprises one functional region (i.e., the second segment) (3) a first polypeptide segment (1), and a third segment (2) that is a polypeptide, one attached to the N-terminus of the functional region and one attached to the C-terminus of the functional region, wherein each surface adsorption region comprises one or more amino sequence motifs and the two surface adsorption regions are the same or different and have the same polarity. (FIG. 3) Either the first polypeptide segment or the third segment is joined to the functional region by a non-peptidic linkage. The purpose of the surface adsorption region(s) is to enable adsorption of the hybrid polypeptide onto an oppositely charged surface in order to build a multilayer film. The purpose of the functional region(s) is to provide specific functionality to the film, such as, for example, a biological function. Other types of function are possible. For example, in one embodiment, the functional region confers on the polypeptide multilayer film the ability to bind calcium divalent cations with a high degree of specificity, as in the case where the functional region is a known calcium binding motif from a protein, e.g., the calcium binding loop of human milk protein α-lactalbumin. There is nothing fundamentally biological about the ability of a multilayer film to bind calcium ions with high specificity, even if some biological macromolecules do exhibit such ability and the peptidic structure, which enables such binding has been engineered into a multilayer film.

A functional region comprises 3 to about 250 amino acid residues. The term functional region includes both functional motifs and functional domains. Functional motifs comprise relatively few amino acid residues and therefore generally do not have a compact or persistent three-dimensional structure; nevertheless, they can exhibit specific functionality, as with some polypeptide hormones and neuropeptides, and they can comprise elements of secondary structure such as α-helices and β-sheets. An example of a functional motif is provided by the RGD sequence of the extracellular matrix protein fibronectin. When the functional unit is a functional motif, it will typically comprise 3 to about 50 amino acid residues. When the functional region is a domain, it will typically comprise about 50 to about 250 amino acid residues.

As used herein, a functional domain typically has a minimum of about 50 amino acid residues and a maximum of about 250 amino acid residues. In principle, any functional domain from a protein can be employed in a composite polypeptide as outlined herein so long as the hybrid composite polypeptide has the appropriate aqueous solubility for ELBL deposition. In one embodiment, the functional domain has a water solubility at pH 4 to 10 of greater than 50 μg/mL. In another embodiment, the functional domain has a water solubility at pH 4 to 10 of greater than or equal to 1 mg/mL. In yet another embodiment, the first layer hybrid composite polypeptide comprises at least two amino acid sequence motifs when the functional unit comprises a functional domain.

The hybrid composite polypeptide, when it comprises a functional motif instead of a functional domain, will typically have an absolute net charge per residue of greater than or equal to 0.4. If the functional motif has a net charge per residue of less than 0.4, the one or more surface adsorption regions will typically have a net charge per residue of greater than 0.4 to compensate and give the hybrid composite polypeptide the appropriate charge properties for solubility and physical adsorption.

Suitable functional regions for inclusion in hybrid composite polypeptides include cysteine-containing motifs or protease recognition sites to control film stability and/or the release of encapsulated materials from films/capsules; T-cell epitopes, B-cell epitopes, or a cytotoxic T lymphocyte epitopes for control of immunogenicity; peptides that are recognized by Toll-like receptors for dendritic cell activation; sequences that occur in protein of the complement system to promote particle opsonization by phagocytes; sequences suitable for attachment of a saccharide or polysaccharide by enzymatic catalysis, for example, as in N-linked or O-linked glycosylation; polypeptide recognition sequences in extracellular matrix proteins for control of surface functionality and tissue engineering; sequences from antibacterial peptides for control of anti-microbial properties; extracellular domains of transmembrane receptors for specific targeting in vivo; and cation binding motifs such as EF hand motifs for control of divalent cation binding.

In one non-limiting embodiment, the functional region of a hybrid composite polypeptide comprises a protease recognition sequence. Suitable protease recognition sequences include, for example, the factor Xa recognition sequence Ile-Glu/Asp-Gly-Arg↓ (SEQ ID NO:1), the enterokinase recognition sequence Asp-Asp-Asp-Asp-Lys↓, (SEQ ID NO:2), the thrombin recognition sequence Leu-Val-Pro-Arg↓Gly-Ser (SEQ ID NO:3), the TEV protease recognition sequence Glu-Asn-Leu-Tyr-Phe-Gln↓Gly (SEQ ID NO:4), the PreScission™ protease recognition sequence Leu-Glu-Val-Leu-Phe-Gln↓Gly-Pro (SEQ ID NO:5), and the like.

In another non-limiting embodiment, the functional region of hybrid composite polypeptide comprises a T-cell epitope, a B-cell epitope, or a cytotoxic T-cell epitope. As used herein, "T-cell epitope" refers to a peptidic antigenic determinant which is recognized by T-cells. As used herein, "B-cell epitope" refers to a peptidic antigenic determinant which is recognized by B-cell immunoglobulin receptors and is capable of eliciting the production of antibodies with appropriate help from T cells when administered to an animal. As used herein, "cytotoxic T lymphocyte epitope" refers to a peptidic antigenic determinant which is recognized by cytotoxic T-lymphocytes. The epitopes are polypeptides produced by viruses, bacteria, fungi, or parasites. In some cases, the epitopes are polypeptides to which saccharides or oligosaccharides are attached or could be attached, e.g., by N-linked or O-linked glycosylation.

Glycosylation is a common and highly diverse protein modification reaction which occurs in most eukaryotic cells. Such modifications are divided into two general categories, N-linked and O-linked. In the former, the carbohydrate moiety is attached to the amide nitrogen of the side chain of asparagine, when asparagine is part of the consensus sequence Asn-X-Ser/Thr. This signal is necessary but not sufficient for glycosylation, e.g., X cannot be Pro, and if Pro occurs shortly downstream of Ser/Thr glycosylation is inhibited. In O-linked glycosylation, the carbohydrate moiety is attached to the hydroxyloxygen of Ser or Thr; it also occurs as a primary modification of tyrosine and a secondary modification of 5-hydroxylysine and 4-hydroxyproline. There is a high frequency of occurrence of Pro, Ser, Thr, and Ala residues around O-linked glycosylation sites.

Linear epitopes are segments composed of a continuous string of amino acid residues along the polymer chain. Typical linear epitopes have a length of about 5 to about 30 amino acids. Conformational epitopes, by contrast, are constituted by two or more sequentially discontinuous segments that are brought together by the folding of the antigen into its native structure. Conformational epitopes generally correspond to longer polypeptide chains than do linear epitopes. Either type of epitope could be present in the functional region of a composite polypeptide for LBL.

In another non-limiting embodiment, the functional region of a hybrid composite polypeptide comprises a sequence from an antimicrobial polypeptide such as an antibacterial polypeptide. Antimicrobial peptides include, for example, inhibitory peptides that slow the growth of a microbe, microbiocidal peptides that are effective to kill a microbe (e.g., bacteriocidal and virocidal polypeptide drugs, sterilants, and disinfectants), and peptides effective for interfering with microbial reproduction, host toxicity, or the like. Examples of antimicrobial peptides include nisin, carnobacteriocins B2 and BM1, leucocin A, mesentericin Y105, sakacins P and A, and curvacin A.

In another non-limiting embodiment, the functional region of a hybrid composite polypeptide is a polypeptide recognition sequence for extracellular matrix (ECM) recognition. One such sequence, RGD, occurs in various extracellular matrix proteins and is a key recognition sequence for integrin transmembrane receptor molecules. Another ECM recognition sequence is GFOGER (SEQ ID NO:6), GLOGER (SEQ ID NO:7), or GASGER (SEQ ID NO:8), wherein 'O' represents hydroxyproline. These are recognition sequences in collagen for collagen-binding integrins. Both types of recognition sequence are suitable for the functional region of a hybrid composite polypeptide for LBL.

In another non-limiting embodiment, the functional region of a hybrid composite polypeptide is a signaling motif for recognition by a cell surface receptor for specific targeting in vivo. The extracellular region of the receptor will bind the polypeptide or protein signal ligand with notable specificity. The polypeptide or protein ligand could be a polypeptide hormone (e.g., insulin, vasopressin, oxytocin) a growth factor (e.g., VEGF, PDGF, FGF), or the like. Such signal sequences are suitable for the functional region of a hybrid composite polypeptide for LBL. In such cases, the functional region of a composite polypeptide for LBL will often be a functional motif. Similarly, the extracellular region of a membrane receptor is suitable for the functional region of a hybrid composite polypeptide for LBL. In such cases, the functional region of a hybrid composite polypeptide for LBL will often be a functional domain.

In another non-limiting embodiment, the functional region of a hybrid composite polypeptide for LBL is a cation binding motif such as an EF hand motif for control of divalent cation binding. Other cation binding domains include the C2 domain, the "VSFASSQQ" (SEQ ID NO:9) motif, and the dockerin domain.

In another non-limiting embodiment, the functional region of a hybrid composite polypeptide is a phosphotyrosine recognition domain, such as a protein tyrosine phosphatase domain, a C2 domain, an SH2 domain, or a phosphotyrosine binding domain. Such domains from numerous different proteins are known to be independent folding units.

In another non-limiting embodiment, the functional domain is a polyproline recognition domain, such as an SH3 domain.

Figure 4:
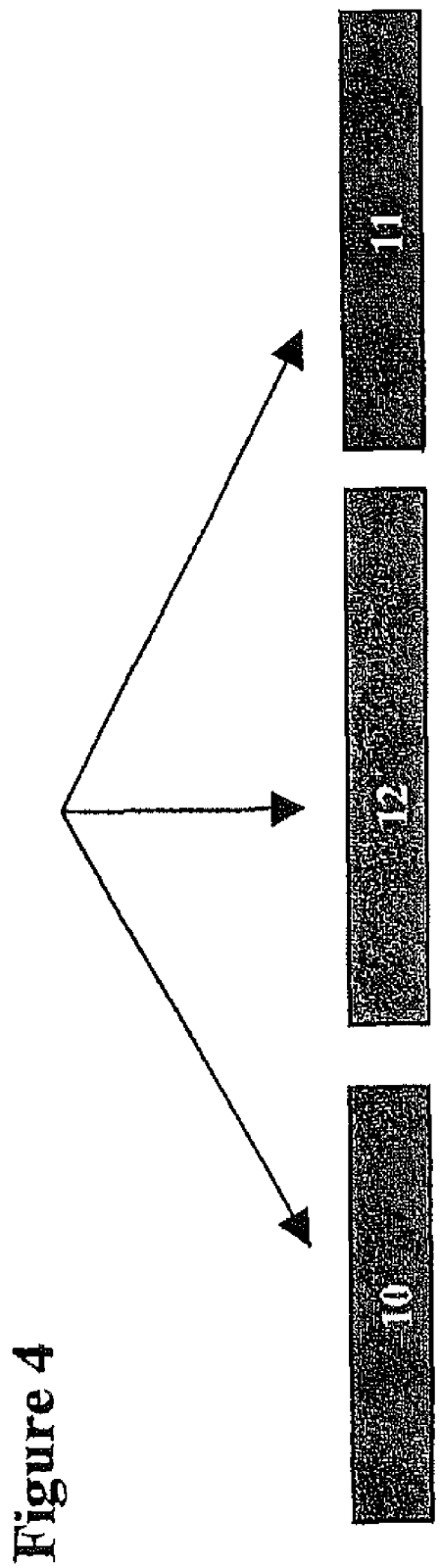
FIG. 4 illustrates an embodiment of the assembly of a hybrid composite polypeptide.

In one embodiment, a first polypeptide segment (10), a third polypeptide segment (11) and a functional region (12) are synthesized separately. (FIG. 4) The three regions are then joined using at least one non-peptidic linker. The solution-phase method can be used to synthesize relatively long peptides and even small proteins. The longest peptides that have made by the solution-phase method are calcitonins (32 mers). More commonly, the method is used to produce small- or medium-length peptides in quantities of up to hundreds of kilograms. It is possible to produce such large quantities of the desired peptides in a facility that follows good manufacturing practices. One or more regions can also be prepared by the solid-phase method. In any case, the three synthesized component peptides are joined using at least one non-peptidic linker.

Figure 5:
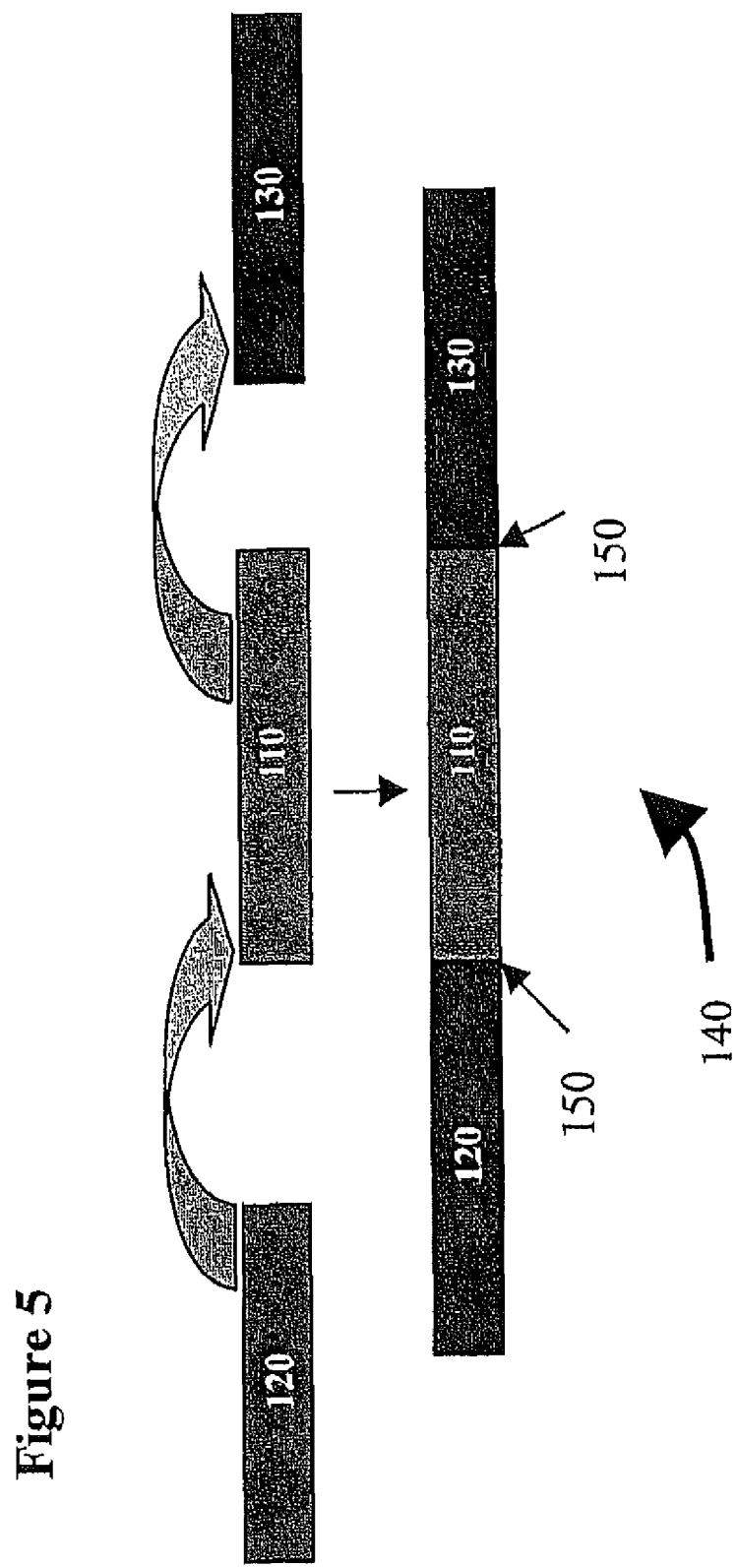
FIG. 5 illustrates an embodiment of a hybrid composite polypeptide.

FIG. 5 illustrates an embodiment of a "hybrid composite" polypeptide comprising a first polypeptide segment (120), a third polypeptide segment (130) and a second segment that is a functional region (110). The first polypeptide segment (120) is located at the N-terminus. The third polypeptide segment (130) is located at the C-terminus. A "hybrid composite" polypeptide is a unique combination of surface adsorption region(s) and functional region(s) in a single polypeptide chain linked by at least one non-peptidic linker. Non-peptidic linkers (150) are used to generate a hybrid composite polypeptide comprising multiple functional regions in a single chain. In one embodiment, functional region (110) can be a small functional region comprising from about 50 to about 130 amino acid residues, and having a diameter of about 2 nm. In an alternate embodiment, functional region (110) can be a large functional region comprising about 250 amino acid residues, and having a diameter of about 4 nm. The length of 16 amino acid residues in extended conformation is approximately 5.5 nm.

Once synthesized, the desired regions are purified, for example, by ion exchange chromatography followed by high-performance liquid chromatography, and then covalently joined using a non-peptidic linker.

An advantage of a modular approach to building hybrid polypeptides includes taking advantage of the previously described amino acid sequence motif technology, minimizing risk. Other advantages include generality of the approach for nearly any conceivable polypeptide sequence. Advantages of synthesizing the hybrid polypeptide segments as individual building blocks include: the ability to pre-make and store practically indefinitely (by lyophilization) the individual building blocks for ready availability; the low cost of production of composite peptides of specific functionality by use of warehoused building blocks prepared in large quantities; the relative simplicity of synthesizing short peptides over long ones, particularly with regard to fidelity of synthesis; rapid preparation of the composite polypeptide in comparison to straight solid-phase, solution-phase or biotic synthesis; rapid response to new developments concerning functional regions due to the modular synthetic approach; and the use of completely synthetic peptides and polypeptide multilayer-based materials as a means of minimizing contamination by microbes and simplifying approval of products by the US Food and Drug Administration.

The hybrid polypeptide comprises one or more non-peptidic chemical linkages. Suitable non-peptidic linkers include, for example, alkyl linkers such as —NH—$(CH_2)_s$—C(O)—, wherein s=2-20. Alkyl linkers are optionally substituted by a non-sterically hindering group such as lower alkyl (e.g., $C_1$-$C_6$), lower acyl, halogen (e.g., Cl, Br), CN, $NH_2$, phenyl, and the like. Another exemplary non-peptidic linker is a poly(ethylene glycol)$_n$ linker, wherein n is such that the linker has a molecular weight of 100 to 5000 kD, specifically 100 to 500 kD. Additional linkers include, for example, adipinic acid hydrazide, bis-succinimidyl-suberate (DSS) and EDTA-hydrazide.

Non-peptidic linkers suitable for amino-amino linking include EGS (Ethylene glycol bis[succinimidylsuccinate]), Sulfo-EGS (Ethylene glycol bis[sulfosuccinimidylsuccinate]), BSOCOES (Bis[2-(succinimidooxycarbonyloxy) ethyl]sulfone), DSP (Dithiobis[succinimidylpropionate]), DTSSP (3,3'-Dithiobis[sulfosuccinimidylpropionate]), DSS (Disuccinimidyl suberate), BS$^3$ (Bis[sulfosuccinimidyl]suberate), DFDNB (1,5-Difluoro-2,4-dinitrobenzene), SFB (Succinimidyl 4-formylbenzoate), DST (Disuccinimidyl tartarate), Sulfo-DST. DiSulfoSuccinimidyl Tartarate, SANH (Succinimidyl 6-.Hydrazinonicotinamide), MSA (Methyl N-succinimidyl adipate), DSG (Disuccinimidyl glutarate), SHTH (Succinimidyl 4-hydrazidoterephthalate.hydrochloride), DMA (dimethyl adipimidate), DMP (dimethyl pimelimidate), DMS (dimethyl suberimidate), DTBP (dimethyl 3,3'-dithiobispropionimidate), C6-SFB (C6-Succinimidyl 4-formylbenzoate), and C6-SANH(C6-Succinimidyl 4-hydrazinonicotinate acetonehydrazone.

Non-peptidic linkers suitable for amino-carboxyl linking include AEDP (3-[(2-Aminoethyl)dithio]propionic acid.HCl), and EDC (1-Ethyl-3-[3-dimethylaminopropyl] carbodiimide Hydrochloride).

Non-peptidic linkers suitable for sulfhydryl-amino crosslinking include SM(PEG)$_{12}$ (Styrene monomer-PEG$_{12}$); SM(PEG)$_8$ (Styrene monomer-PEG$_8$); SM(PEG)$_4$ (Styrene monomer-PEG$_4$); SMPT (4-Succinimidyloxycarbonyl-methyl-a-[2-pyridyldithio]toluene); Sulfo-LC-SMPT (4-Sulfosuccinimidyl-6-methyl-a-(2-pyridyldithio)toluamido]hexanoate)); SM(PEG)$_2$ (Styrene monomer-PEG$_2$); Sulfo-KMUS (N-[k-Maleimidoundecanoyloxy]sulfosuccinimide ester); LC-SMCC (Succinimidyl-4-[N-Maleimidomethyl] cyclohexane-1-carboxy-[6-amidocaproate]); KMUA (N-k-Maleimidoundecanoic acid); Sulfo-KMUS (N-[k-Maleimidoundecanoyloxy]sulfosuccinimide ester); Sulfo-LC-SPDP (Sulfosuccinimidyl 6-(3'-[2-pyridyldithio]-propionamido) hexanoate); LC-SPDP (Succinimidyl 6-(3-[2-pyridyldithio]-propionamido)hexanoate); SMPH (Succinimidyl-6-[β-maleimidopropionamido]hexanoate); SMPB (Succinimidyl 4-[p-maleimidophenyl]butyrate); Sulfo-SMPB (Sulfosuccinimidyl 4-[p-maleimidophenyl]butyrate); Sulfo-SIAB (N-Sulfosuccinimidyl[4-iodoacetyl]aminobenzoate); STAB (N-Succinimidyl[4-iodoacetyl]aminobenzoate); Sulfo-EMCS ([N-e-Maleimidocaproyloxy]sulfosuccinimide ester); EMCA (N-e-Maleimidocaproic acid); EMCS ([N-e-Maleimidocaproyloxy]succinimide ester); EMCS ([N-e-Maleimidocaproyloxy]succinimide ester); Sulfo-SMCC (Sulfosuccinimidyl 4-[N-maleimidomethyl]cyclohexane-1-carboxylate); Sulfo-MBS (m-Maleimidobenzoyl-N-hydroxysulfosuccinimide ester); Sulfo-GMBS (N-[g-Maleimidobutyryloxy]sulfosuccinimide ester); MBS (m-Maleimidobenzoyl-N-hydroxysuccinimide ester); GMBS (N-[g-Maleimidobutyryloxy]succinimide ester); SPDP (N-Succinimidyl 3-[2-pyridyldithio]-propionamido); SBAP (Succinimidyl 3-[bromoacetamido]propionate); BMPS(N-[β-Maleimidopropyloxy]succinimide ester); BMPA (N-β-Maleimidopropionic acid); AMAS N-(a-Maleimidoacetoxy) succinimide ester); SIA (N-Succinimidyl iodoacetate); and SATP (N-succinimidyl S-acetylthiopropionate).

The chemistry used to join the first polypeptide segment and second segment depends upon the desired linkage group on the first polypeptide segment and second segment and the non-peptidic linkage.

Figure 6:
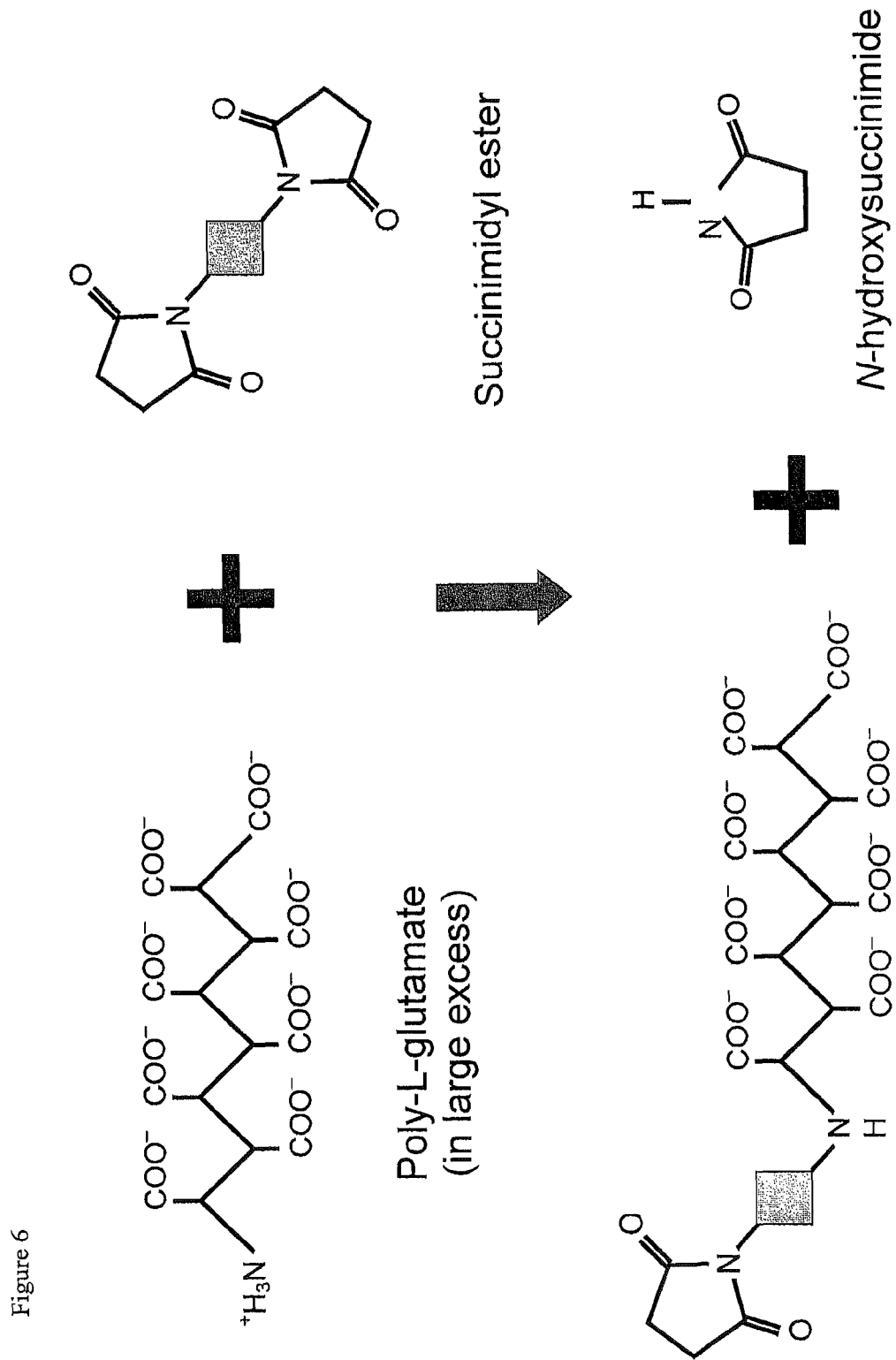
FIG. 6 illustrates the reaction of a first polypeptide segment with a succinimidyl ester linker.
Figure 7:
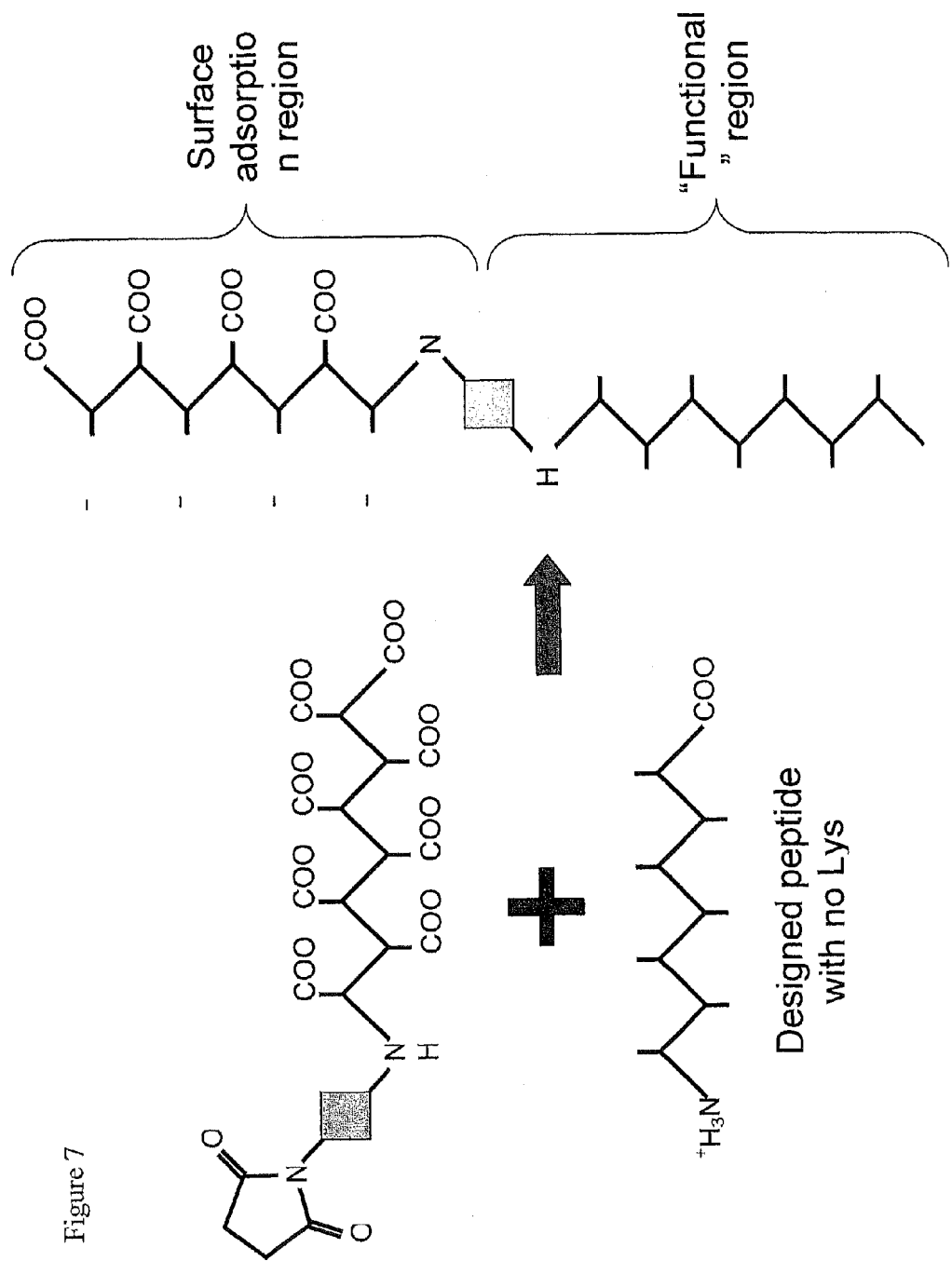
FIG. 7 illustrates the reaction of the first polypeptide segment comprising a linker with a second polypeptide segment to form a hybrid polypeptide.

A particularly useful approach for forming a hybrid polypeptide comprising a first polypeptide segment and a second polypeptide segment, wherein the second polypeptide segment is a functional region and the first polypeptide segment is a surface adsorption region and has no basic side chains, is the following. Disuccinimidyl glutarate (DSG) is reacted in large excess with the first polypeptide segment. The resulting product is DSG joined to the N-terminal amino group of the first polypeptide segment, that is, a DSG-first polypeptide segment conjugate. (FIG. 6) DSG does not react with any side chains in this case; DSG reacts with a free amino group. Unreacted DSG is then separated from the DSG-first polypeptide segment conjugate by an appropriate method, for example, gel filtration. The DSG-first polypeptide segment conjugate is then reacted with the second polypeptide segment. The reaction is straight-forward if the second polypeptide segment contains one free amino group only—at the N-terminus. In this case, the hybrid polypeptide is separated from non-hybrid polypeptide by an appropriate method, for example, gel filtration. If the second polypeptide segment contains an amino group in the side chain, however, it may be necessary to block the side chain amino groups until after the reaction between the DSG-first peptide segment conjugate and the second peptide segment has gone to completion. Side chain amino groups can be blocked by trifluoroacetic acid (TFA). In general, the reaction between the DSG-first—polypeptide segment conjugate and the second polypeptide segment can be carried out before the side chains of the second polypeptide segment have been deprotected following synthesis of the second polypeptide segment.

The invention is further illustrated by the following non-limiting examples.

EXAMPLES

Example 1

Hybrid Polypeptide Comprising a First and a Second Polypeptide Segment

The polypeptide sequence ISQAVHAAHAEINEAGR (SEQ ID NO:10), an immunodominant epitope of chicken ovalbumin in mouse, is prepared by solid-phase synthesis. This is the second polypeptide segment of the hybrid polypeptide, and is a functional motif. No lysine residue is present in the peptide. The first polypeptide segment, or surface adsorption region, is poly(glutamic acid). Poly(glutamic acid) is readily prepared separately by solution-phase synthesis. The poly(glutamic acid) synthesis product will generally be highly heterogeneous, not in sequence, but in molecular weight species. Fractionation of such species during purification, for example, by gel filtration, enables separation of the poly(glutamic acid) chains into successive ranges of molecule e.g., 2,500-5,000 Da. Such material is then joined at the N-terminus to DST, forming a DST-poly(glutamic acid) conjugate. The reaction is carried out for 30 min in reaction buffer (e.g., 20 mM phosphate, 0.15 M sodium chloride, pH 8; HEPES, bicarbonate/carbonate, or borate buffer, pH 7-9). Immediately before use, DST is dissolved in DMSO at 10-25 mM, and DST is added to a final concentration of 1-5 mM. The reaction is quenched by incubating Tris at a final concentration of 10-20 mM for 15 min at room temperature. Unreacted DST linker is separated from the DST-poly(glutamic acid) conjugate by, for example, gel filtration. The DST-poly (glutamic acid) conjugate is then reacted with the ovalbumin polypeptide, forming a hybrid polypeptide. Any unreacted polypeptide is separated from the hybrid polypeptide by an appropriate chromatographic method.

Example 2

Hybrid Polypeptide Comprising a First and a Second Polypeptide Segment

The peptide FEPSEAEISHTQKA (SEQ ID NO:11), from a human T cell receptor, is prepared by solid-phase synthesis. This is the second polypeptide segment of the hybrid polypeptide, and is a functional motif. The DST-poly (glutamic acid) conjugate of Example 1 is then reacted with the T cell receptor polypeptide. The lysine side chain in this peptide is protected during the reaction with the DST-poly (glutamic acid) conjugate. Following conjugation of the DST-poly(glutamic acid) conjugate to the T cell receptor peptide, the lysine side chain of the T cell receptor polypeptide is deprotected, leaving the desired hybrid polypeptide.

Example 3

Hybrid Polypeptide Comprising a First and a Second Polypeptide Segment

The human T cell receptor peptide (SEQ ID NO:11) of Example 2 is reacted with DSG-poly(glutamic acid) in place of DST-poly(glutamic acid). DSG or DST is selected on the basis of the desired linker length.

Example 4

Hybrid Polypeptide Comprising a First and a Second Polypeptide Segment

In another related example, the human T cell receptor peptide (SEQ ID NO: 11) of Example 2 is reacted with an ethylene glycol linker, for example, EGS. The two functional groups of this linker are the same as for DSG and DST, namely, succinimidylsuccinate groups; the chemistry is the same, the structure of the linker is different.

Example 5

Hybrid Polypeptide Comprising a First and a Second Polypeptide Segment

The peptide ECESAETTED (SEQ ID NO: 12), from mouse serum albumin, is prepared by solid-phase synthesis. This is the second polypeptide segment of the hybrid polypeptide, and is a functional motif. The thiol group in the cysteine side chain enables formation of a hybrid polypeptide in several ways: crosslinking by direct disulfide bond formation between peptides in the absence of a crosslinking molecule; crosslinking to poly(glutamic acid) by means of DSG or DST as in the foregoing examples; and crosslinking to poly(glutamic acid) by means of a crosslinker that can react with the free sulfhydryl in the serum albumin peptide and the free amino group in poly(glutamic acid). Some suitable linker molecules for the last of these possibilities feature a free sulfhydryl group and a succinimide group. Two of the many possible examples of such molecules include sulfo-KMUS, (N-[k-maleimidoundecanoyloxy]sulfosuccinimide ester) and sulfo-SMPB, (sulfosuccinimidyl 4-[p-maleimidophenyl] butyrate).

Example 6

Hybrid Polypeptide Comprising a First Polypeptide Segment and a Second Polynucleotide Segment The peptide EEEEEEEEECEEEEEEEE (SEQ ID NO: 13), the first polypeptide segment, is used to form a hybrid polypeptide with a second segment comprising double-stranded DNA, one strand of which has the sequence 5'-ACTCGCGCGCGCGCGCGCCACT-3' (SEQ ID NO: 14). A suitable non-peptidic linker is PMPI, (N-[p-maleimidophenyl]isocyanate), which has both hydroxyl and sulfhydryl reactivity. The sulfhydryl reactivity is used to conjugate the linker first to the first polypeptide segment. The hydroxyl reactivity in the PMPI linker is used to conjugate the linker-peptide to the second DNA segment via the 3'-end hydroxyl group of the DNA. The same approach can be used for single-stranded DNA or RNA, as a free hydroxyl group is present at the 3'-end of the molecule in each case. This construct could readily be incorporated into a polypeptide multilayer film, and the nucleic acid could be used to activate dendritic cells via a Toll-like receptor sensitive to certain DNA sequences.

Example 7

Hybrid Polypeptide Comprising a First Polypeptide Segment and a Second Polysaccharide Segment The first polypeptide segment of Example 6 (SEQ ID NO: 13) is used to form a hybrid polypeptide with a second segment comprising a polysaccharide that is recognized by a cell surface receptor, e.g., a high-mannose polysaccharide. A suitable non-peptidic linker is KMUH, (N-[k-maleimidoundecanoic acid]hydrazide), a sulfhydryl-reactive and carbonyl-reactive heterobifunctional crosslinking reagent for glycoconjugate preparation. Maleimide reacts with —SH groups at pH 6.5-7.5, forming a stable thioether. The hydrazide group covalently couples to an oxidized carbohydrate residue. The linker is joined first to the peptide and then to the polysaccharide. This construct could readily be incorporated into a polypeptide multilayer film, and the nucleic acid could be used to activate dendritic cells via a Toll-like receptor sensitive to certain polysaccharide sequences.

Example 8

Hybrid Polypeptide Comprising a First Polypeptide Segment and a Second Fatty Acid Segment The first polypeptide segment of Example 1 (SEQ ID NO:10) is used to form a hybrid polypeptide with a second segment comprising myristic acid, a fatty acid that is often found attached to the N-terminus of plasma membrane-associated cytoplasmic proteins. The zero-length crosslinking agent EDC (1-ethyl-3-[3-dimethylaminopropyl]carbodiimide hydrochloride) is used to couple the primary amino group of the peptide to the carboxyl group of myristic acid. EDC is reacted with the carboxyl group on myristic acid, forming an amino-reactive O-acylisourea intermediate. Addition of Sulfo-NHS stabilizes the amine-reactive intermediate, which reacted with the peptide. The hybrid polypeptide can be incorporated in a polypeptide multilayer nanocapsules, and the presence of myristic acid can be used to associate the nanocapsule with the cell membrane.

Example 9

Hybrid Polypeptide Comprising a First Polypeptide Segment and a Second Small Molecule Segment The first polypeptide segment KKKKKKKKKKKKKKK (SEQ ID NO: 15) is used to form a hybrid polypeptide with a second segment comprising Ellman's reagent (DTNB) (5-5'-dithiobis-(2-nitrobenzoic acid)), a symmetric aryl disulfide. The crosslinking agent SM(PEG)$_4$ (Styrene monomer-PEG$_4$) is coupled to either the amino group of the N-terminal residue or the amino group of any of the lysine side chains, and the free thiol of this intermediate reacts with DTNB to give a mixed disulfide plus 2-nitro-5-thiobenzoic acid (TNB). The hybrid polypeptide can be incorporated in a polypeptide multilayer nanocapsules, and the release of TNB can be stimulated by a change in redox potential.

Example 10

Hybrid Polypeptide Comprising a First Polypeptide Segment and a Second Polypeptide Segment which is Biotinylated A first polypeptide segment KKKKKKKKKKKKKKK (SEQ ID NO: 15) is used to form a hybrid polypeptide with a second polypeptide segment, the first polypeptide segment of Example 1, which has been biotinylated on the N-terminus. The zero-length crosslinking agent EDC (1-ethyl-3-[3-dimethylaminopropyl]carbodiimide hydrochloride) is used to couple the primary amino group of the first peptide segment to the C-terminus of the second polypeptide segment or the carboxyl group of either glutamic acid side chain. The hybrid polypeptide can be incorporated into a polypeptide multilayer nanocapsule. The biotinylated N-terminus of the second polypeptide segment can bind strongly to avidin, enable the nanocapsule to bind tightly to any surface onto which avidin is immobilized.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A multilayer film, said film comprising two or more layers of polyelectrolytes, wherein adjacent layers comprise oppositely charged polyelectrolytes,
   wherein the first layer polyelectrolyte comprises a hybrid polypeptide comprising a first polypeptide segment and a second polypeptide segment covalently joined by one or more non-peptidic linkages;
   wherein the first polypeptide segment comprises a polypeptide having a magnitude of net charge per residue of greater than or equal to 0.4, and a length of greater than or equal to about 12 amino acid residues;
   wherein the second polypeptide segment comprises a functional region comprising 3 to about 250 amino acids selected from the group consisting of a cysteine-containing sequence, a sequence for extracellular matrix recognition, a phosphotyrosine binding domain, a Src homology 2 domain, an N-linked glycosylation substrate sequence, an O-linked glycosylation substrate sequence, a protease recognition site, an antimicrobial peptide sequence, a BAG domain, a T-cell epitope, or a combination thereof;
   wherein the N-terminus of the first polypeptide segment is joined to the C-terminus of the second polypeptide segment, the N-terminus of the first polypeptide segment is joined to the N-terminus of the second polypeptide segment, the C-terminus of the first polypeptide segment is joined to the C-terminus of the second polypeptide segment, or the C-terminus of the first polypeptide segment is joined to the N-terminus of the second polypeptide segment by the one or more non-peptidic linkages; and
   wherein the second layer polyelectrolyte comprises a polycationic material or a polyanionic material having a molecular weight of greater than 1,000, at least 5 charges per molecule, and a charge opposite that of the first layer polypeptide.

2. The multilayer film of claim 1, wherein the hybrid polypeptide has an aqueous solubility at pH 4 to 10 of greater than 50 μg/mL.

3. The multilayer film of claim 1, wherein the aqueous solubility of the hybrid polypeptide at pH 4 to 10 is greater than or equal to about 1 mg/mL.

4. The multilayer film of claim 1, wherein the hybrid polypeptide comprises a third segment, wherein the third segment comprises a polypeptide segment having a magnitude of net charge per residue of greater than or equal to 0.4, and a length of greater than or equal to about 12 amino acid residues.

5. The multilayer film of claim 1, wherein the film is in the form of a microcapsule.

6. The multilayer film of claim 5, wherein the microcapsule comprises a core, and the core comprises a protein, a drug, or a combination thereof.

7. The multilayer film of claim 6, wherein the protein or drug is in crystallized form.

8. The multilayer film of claim 6, wherein the protein or drug is in liquid form.

9. The multilayer film of claim 1, comprising at least 4 pairs of alternately charged layers.

10. The multilayer film of claim 1, having a thickness of 1 nm to 100 nm.

11. The multilayer film of claim 1, wherein the film is formed on a substrate.

12. The multilayer film of claim 11, wherein the film comprises a medical device.

13. The multilayer film of claim 1, wherein the non-peptidic linkage comprises disuccinimidyl glutarate, disuccinimidyl tartarate, N-[k-maleimidoundecanoyloxy]sulfosuccinimide ester), (sulfosuccinimidyl 4-[p-maleimidophenyl] butyrate), (N-[p-maleimidophenyl]isocyanate), (1-ethyl-3-[3-dimethylaminopropyl]carbodiimide hydrochloride), Styrene monomer-PEG$_4$, or (N-[k-maleimidoundecanoic acid]hydrazide).

14. The multilayer film of claim 1, wherein the hybrid polypeptide is a non-branched polypeptide.

\* \* \* \* \*